(12) United States Patent
Biedermann et al.

(10) Patent No.: US 11,717,329 B2
(45) Date of Patent: Aug. 8, 2023

(54) COUPLING DEVICE FOR COUPLING A ROD TO A BONE ANCHORING ELEMENT AND METHOD OF MANUFACTURING THE SAME

(71) Applicant: BIEDERMANN TECHNOLOGIES GMBH & CO. KG, Donaueschingen (DE)

(72) Inventors: Timo Biedermann, Trossingen (DE); Bernd Fischer, Bräunlingen (DE); Tobias Hägle, Donaueschingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/879,685

(22) Filed: Aug. 2, 2022

(65) Prior Publication Data

US 2023/0039136 A1 Feb. 9, 2023

Related U.S. Application Data

(60) Provisional application No. 63/229,231, filed on Aug. 4, 2021.

(30) Foreign Application Priority Data

Aug. 4, 2021 (EP) .................................... 21189722

(51) Int. Cl.
*A61B 17/70* (2006.01)
*A61B 17/00* (2006.01)
*A61B 17/56* (2006.01)

(52) U.S. Cl.
CPC ...... *A61B 17/7037* (2013.01); *A61B 17/7032* (2013.01); *A61B 2017/00526* (2013.01); *A61B 2017/564* (2013.01)

(58) Field of Classification Search
CPC . A61B 17/70; A61B 17/7032; A61B 17/7035; A61B 17/7037
See application file for complete search history.

(56) References Cited

U.S. PATENT DOCUMENTS 5,584,834 A * 12/1996 Errico ................ A61B 17/7037
606/264
5,586,984 A * 12/1996 Errico ................ A61B 17/7037
606/264

(Continued)

FOREIGN PATENT DOCUMENTS

EP 2 668 919 A1 12/2013

OTHER PUBLICATIONS

Extended European Search Report for Application No. 21189722.8, dated Feb. 9, 2022, 9 pages.

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A coupling device for coupling a rod to a bone anchoring element includes a receiving part with a head receiving portion for receiving a head of the bone anchoring element, a rod receiving portion for receiving the rod, a downwardly facing surface, and an upwardly facing surface below and monolithically formed with the downwardly facing surface, and a locking member movable relative to the receiving part from a first position where the head is insertable into the head receiving portion to a second position where the head is prevented from being removed from the head receiving portion. At least part of the locking member is held to the receiving part between the downwardly and upwardly facing surfaces, and wherein the receiving part and the locking member are only separable from one another by perma- (Continued)

nently deforming or damaging at least one of the receiving part or the locking member.

20 Claims, 13 Drawing Sheets

(56) References Cited

U.S. PATENT DOCUMENTS

| | | | | |
|---|---|---|---|---|
| 6,248,105 B1* | 6/2001 | Schlapfer | ............ | A61B 17/7037 606/272 |
| 6,254,602 B1* | 7/2001 | Justis | ............... | A61B 17/7037 606/53 |
| 6,273,888 B1* | 8/2001 | Justis | ............... | A61B 17/7037 606/911 |
| 9,339,302 B2 | 5/2016 | Biedermann et al. | | |
| 9,615,862 B1* | 4/2017 | Doubler | ............. | A61B 17/7076 |
| 10,285,738 B1* | 5/2019 | Doubler | ............. | A61B 17/7037 |
| 11,006,981 B2 | 5/2021 | Melton et al. | | |
| 11,020,150 B1* | 6/2021 | Doubler | ............. | A61B 17/7032 |
| 11,141,199 B1* | 10/2021 | Doubler | ............. | A61B 17/7032 |
| 11,333,192 B1* | 5/2022 | Lentner | ............... | F16C 11/069 |
| 2002/0032443 A1* | 3/2002 | Sherman | ............ | A61B 17/7032 606/264 |
| 2005/0080415 A1* | 4/2005 | Keyer | ............... | A61B 17/7037 606/279 |
| 2005/0080420 A1* | 4/2005 | Farris | ............... | A61B 17/7038 606/328 |
| 2005/0228392 A1* | 10/2005 | Keyer | ............... | A61B 17/7086 606/86 R |
| 2006/0161152 A1* | 7/2006 | Ensign | ............... | A61B 17/7032 606/279 |
| 2007/0233087 A1* | 10/2007 | Schlapfer | ............ | A61B 17/7035 606/232 |
| 2008/0004625 A1* | 1/2008 | Runco | ............... | A61B 17/7037 606/273 |
| 2008/0108992 A1* | 5/2008 | Barry | ............... | A61B 17/7037 606/103 |
| 2009/0036934 A1* | 2/2009 | Biedermann | ...... | A61B 17/7037 606/301 |
| 2009/0069852 A1* | 3/2009 | Farris | ............... | A61B 17/7038 606/301 |
| 2009/0149887 A1* | 6/2009 | Schlaepfer | .......... | A61B 17/7091 606/301 |
| 2009/0182380 A1* | 7/2009 | Abdelgany | ........ | A61B 17/7037 606/301 |
| 2010/0087873 A1* | 4/2010 | Null | ................... | A61B 17/7034 606/305 |
| 2010/0125302 A1* | 5/2010 | Hammill, Sr. | ...... | A61B 17/7035 606/301 |
| 2010/0137920 A1* | 6/2010 | Hammill, Sr. | ...... | A61B 17/7037 606/308 |
| 2010/0145394 A1* | 6/2010 | Harvey | .............. | A61B 17/7049 606/305 |
| 2010/0160975 A1* | 6/2010 | Biedermann | ...... | A61B 17/7037 606/305 |
| 2010/0160976 A1* | 6/2010 | Biedermann | ...... | A61B 17/7035 606/305 |
| 2010/0168800 A1* | 7/2010 | Biedermann | ...... | A61B 17/7037 606/305 |
| 2010/0168801 A1* | 7/2010 | Biedermann | ...... | A61B 17/7037 606/302 |
| 2010/0204735 A1* | 8/2010 | Gephart | ............. | A61B 17/7082 606/279 |
| 2010/0305620 A1* | 12/2010 | Gotfried | ............ | A61B 17/7037 606/328 |
| 2010/0312288 A1* | 12/2010 | Hammill, Sr. | ...... | A61B 17/7037 606/305 |
| 2011/0009911 A1* | 1/2011 | Hammill, Sr. | ...... | A61B 17/7038 606/308 |
| 2011/0040336 A1* | 2/2011 | Hammill, Sr. | ...... | A61B 17/7037 606/305 |
| 2011/0276098 A1* | 11/2011 | Biedermann | ...... | A61B 17/7037 606/1 |
| 2012/0016425 A1* | 1/2012 | Shaffrey | ............ | A61B 17/7056 606/305 |
| 2012/0046699 A1* | 2/2012 | Jones | ................. | A61B 17/7037 606/305 |
| 2012/0095516 A1* | 4/2012 | Dikeman | ............ | A61B 17/7037 606/305 |
| 2012/0109218 A1* | 5/2012 | Farris | ................ | A61B 17/7032 606/305 |
| 2012/0165874 A1* | 6/2012 | Biedermann | ...... | A61B 17/7037 606/279 |
| 2012/0172932 A1* | 7/2012 | Biedermann | ...... | A61B 17/7037 606/279 |
| 2012/0179209 A1* | 7/2012 | Biedermann | ...... | A61B 17/7037 606/279 |
| 2012/0179211 A1* | 7/2012 | Biedermann | ...... | A61B 17/7037 606/279 |
| 2012/0197314 A1* | 8/2012 | Farris | ................ | A61B 17/7037 606/305 |
| 2012/0209335 A1* | 8/2012 | Termyna | ............ | A61B 17/7037 606/300 |
| 2012/0232598 A1* | 9/2012 | Hestad | .............. | A61B 17/7037 29/446 |
| 2013/0085536 A1* | 4/2013 | Biedermann | ...... | A61B 17/7035 606/328 |
| 2013/0096623 A1* | 4/2013 | Biedermann | ...... | A61B 17/7037 606/279 |
| 2013/0123860 A1* | 5/2013 | Biedermann | ...... | A61B 17/8685 606/86 R |
| 2013/0150852 A1* | 6/2013 | Shluzas | .............. | A61B 17/7001 606/65 |
| 2013/0338721 A1* | 12/2013 | Biedermann | ...... | A61B 17/7034 606/305 |
| 2014/0012337 A1* | 1/2014 | Biedermann | ........ | A61B 17/844 606/328 |
| 2014/0025120 A1* | 1/2014 | Farris | ................ | A61B 17/7035 606/300 |
| 2014/0031880 A1* | 1/2014 | Biedermann | ...... | A61B 17/7035 606/305 |
| 2015/0032162 A1* | 1/2015 | Biedermann | ...... | A61B 17/7035 606/278 |
| 2015/0119940 A1* | 4/2015 | Jackson | ............. | A61B 17/7076 606/266 |
| 2015/0134006 A1* | 5/2015 | Ziolo | ................. | A61B 17/7035 606/278 |
| 2015/0201972 A1* | 7/2015 | Doubler | ............. | A61B 17/7002 606/266 |
| 2015/0250512 A1* | 9/2015 | Poker | ................. | A61B 17/7082 606/305 |
| 2016/0030090 A1* | 2/2016 | Webb | ................. | A61B 17/7037 606/266 |
| 2016/0166288 A1* | 6/2016 | Biedermann | ...... | A61B 17/7037 606/272 |
| 2017/0020574 A1* | 1/2017 | Biedermann | ...... | A61B 17/7032 |
| 2017/0112542 A1* | 4/2017 | Biedermann | ...... | A61B 17/7035 |
| 2017/0245898 A1* | 8/2017 | May | .................... | A61B 17/7032 |
| 2017/0367843 A1 | 12/2017 | Eisen et al. | | |
| 2017/0367845 A1 | 12/2017 | Eisen et al. | | |
| 2018/0036039 A1* | 2/2018 | Biedermann | ...... | A61B 17/7037 |
| 2018/0055542 A1* | 3/2018 | Biedermann | ...... | A61B 17/7083 |
| 2018/0055545 A1* | 3/2018 | Biedermann | ...... | A61B 17/7032 |
| 2018/0092670 A1* | 4/2018 | Crossgrove | ........ | A61B 17/7032 |
| 2018/0153588 A1* | 6/2018 | Mosnier | ............. | A61B 17/7037 |
| 2019/0117270 A1* | 4/2019 | Biedermann | ...... | A61B 17/7076 |
| 2019/0175224 A1* | 6/2019 | Doubler | ............. | A61B 17/7002 |
| 2019/0192192 A1* | 6/2019 | Biedermann | ...... | A61B 17/7037 |
| 2019/0209214 A1* | 7/2019 | Biedermann | ...... | A61B 17/7037 |
| 2019/0223917 A1* | 7/2019 | Gray | .................. | A61B 17/7082 |
| 2019/0274737 A1* | 9/2019 | Biedermann | ...... | A61B 17/7032 |
| 2020/0022772 A1* | 1/2020 | Benson | .............. | A61B 5/4851 |
| 2020/0146724 A1* | 5/2020 | Italiaie | ............... | A61B 17/7032 |
| 2020/0229847 A1* | 7/2020 | Capote | .............. | A61B 17/7037 |
| 2020/0360067 A1* | 11/2020 | Simpson | ............ | A61B 17/8685 |
| 2021/0015521 A1* | 1/2021 | Biedermann | ...... | A61B 17/7032 |
| 2021/0052305 A1* | 2/2021 | Dong | ................. | A61B 17/7032 |
| 2021/0114298 A1 | 4/2021 | Rodriguez Santiago et al. | | |

(56) References Cited

U.S. PATENT DOCUMENTS

| | | | |
|---|---|---|---|
| 2021/0145485 A1* | 5/2021 | Biedermann | A61B 17/7037 |
| 2021/0186569 A1* | 6/2021 | Biedermann | A61B 17/7046 |
| 2021/0186575 A1* | 6/2021 | Biedermann | A61B 17/7037 |
| 2021/0330362 A1* | 10/2021 | Biedermann | A61B 17/7032 |
| 2021/0369315 A1* | 12/2021 | Heuer | A61B 17/7037 |
| 2021/0401466 A1* | 12/2021 | Biedermann | A61B 17/7032 |
| 2022/0133358 A1* | 5/2022 | Biedermann | A61B 17/7002 606/278 |
| 2022/0160401 A1* | 5/2022 | Biedermann | A61B 17/7086 |
| 2022/0168024 A1* | 6/2022 | Biedermann | A61B 17/7076 |
| 2022/0330988 A1* | 10/2022 | Biedermann | A61B 17/7082 |

\* cited by examiner

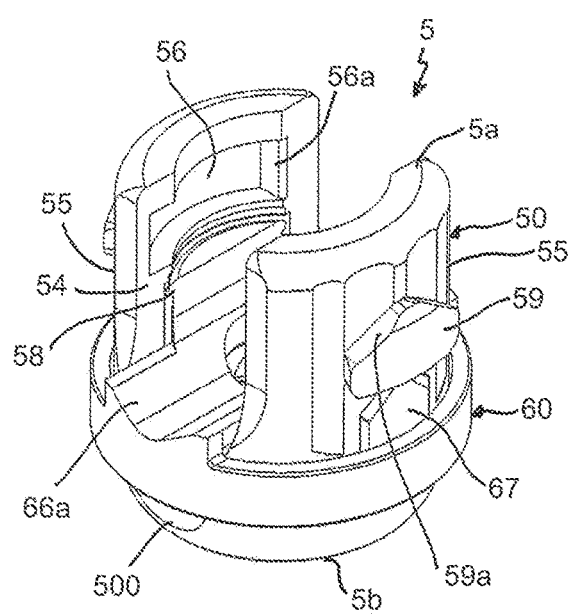
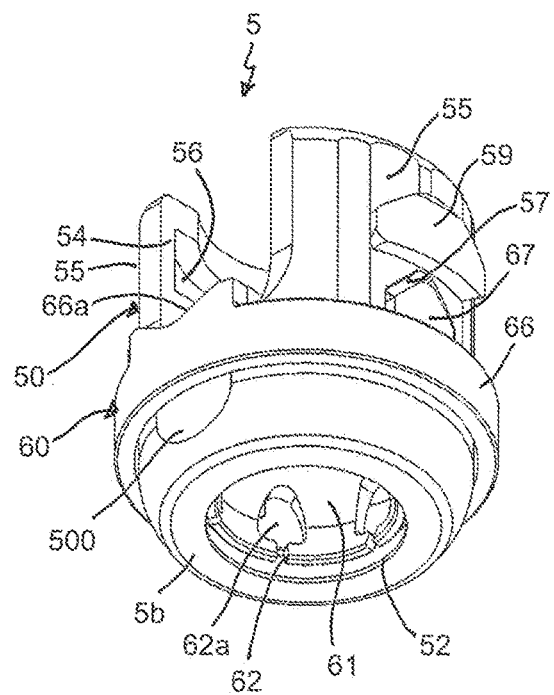
Fig. 4
Fig. 5
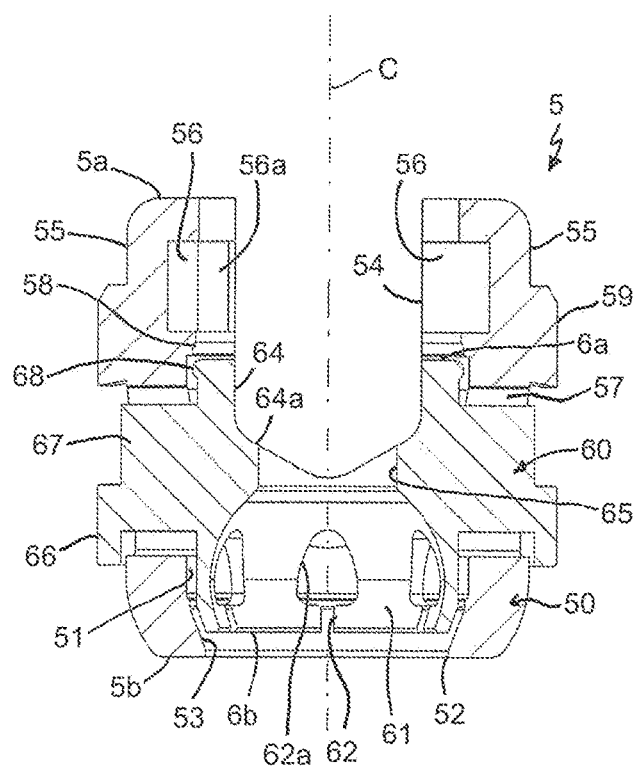
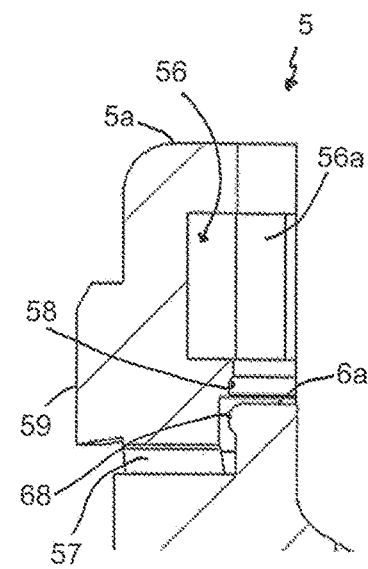
Fig. 6a
Fig. 6b

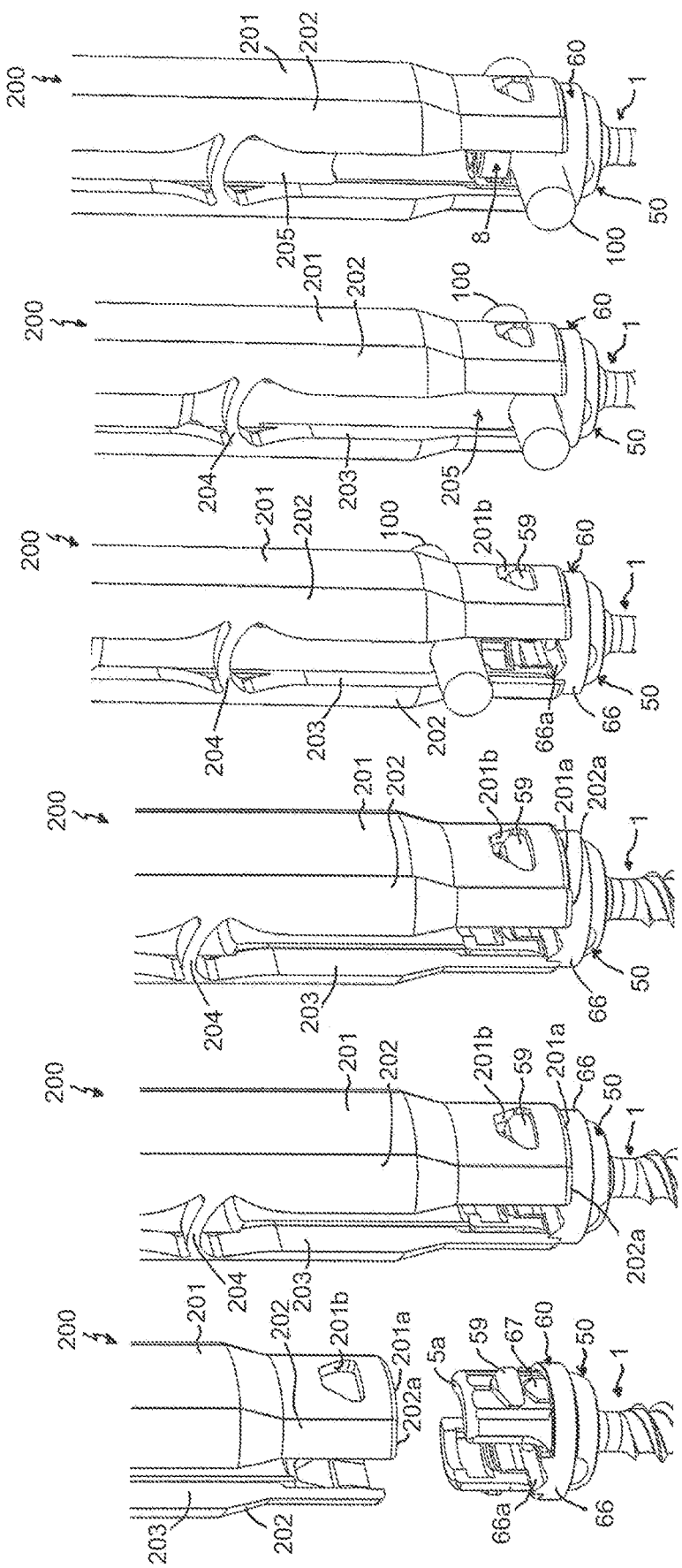

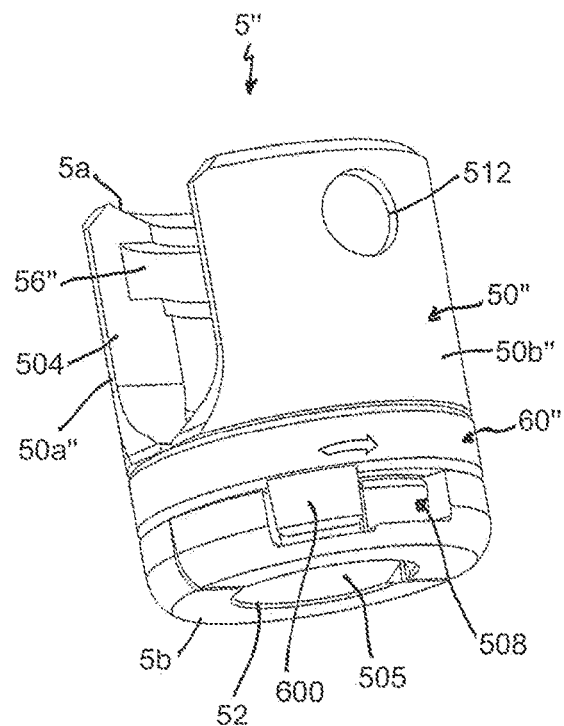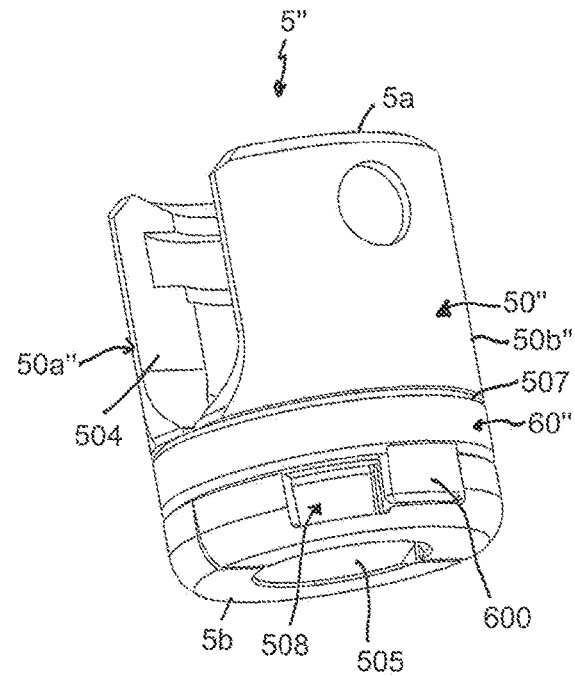
Fig. 21    Fig. 22
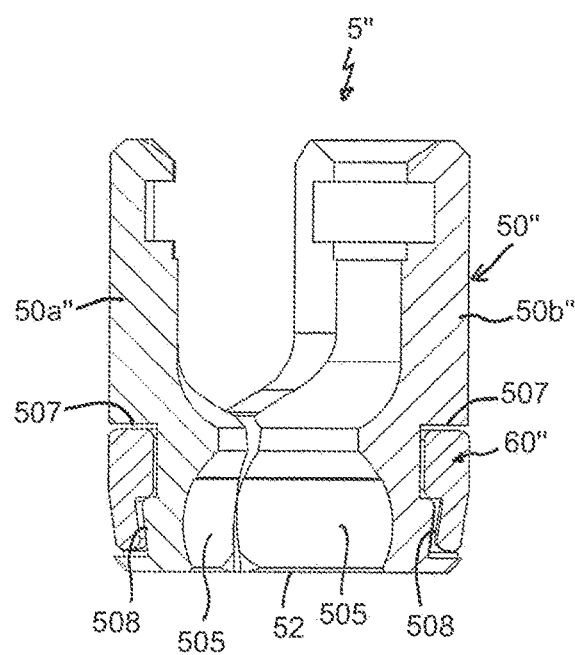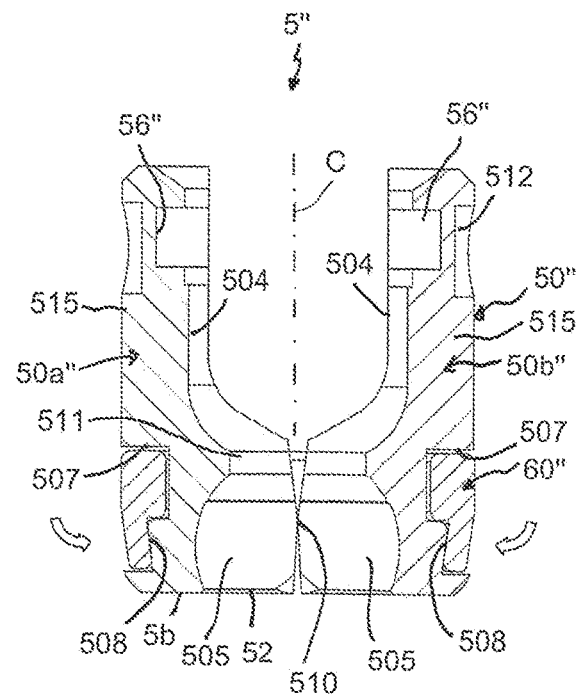
Fig. 23    Fig. 24

COUPLING DEVICE FOR COUPLING A ROD TO A BONE ANCHORING ELEMENT AND METHOD OF MANUFACTURING THE SAME

CROSS-REFERENCE TO RELATED APPLICATION(S)

The present application claims priority to and the benefit of U.S. Provisional Patent Application No. 63/229,231, filed Aug. 4, 2021, the contents of which are hereby incorporated by reference in their entirety, and claims priority from European Patent Application EP 21 189 722.8, filed Aug. 4, 2021, the contents of which are hereby incorporated by reference in their entirety.

BACKGROUND

Field

The application relates to a coupling device for coupling a rod to a bone anchoring element and to methods of manufacturing and using the same. In particular, the invention relates to a coupling device that forms part of a polyaxial bone anchoring device.

Description of Related Art

Various types of polyaxial bone anchoring devices are known in the art. Usually, a polyaxial bone anchoring device includes a coupling device and a bone anchoring element with a head that is pivotably received in the coupling device and that can be locked at a desired angle relative to the coupling device. The coupling device also receives a rod that is configured to connect the polyaxial bone anchoring device to a further bone anchoring device. U.S. Pat. No. 9,339,302 B2, for example, describes such a polyaxial bone anchoring device. The document also describes a two-part locking member for a polyaxial bone anchoring device that is manufactured using an additive manufacturing method. The two-part locking device is made as a monolithic piece including predetermined breaking areas that break when a certain torque is applied. Thereby the parts become separated.

US 2017/0367843 A1 describes various interbody fusion spacers or cages for insertion between adjacent vertebrae. The implantable devices may be manufactured using a selective laser melting (SLM) technique, a form of additive manufacturing. By means of this, intervertebral cages are formed of multiple, interconnected parts that do not require additional external fixation elements to keep together.

U.S. Pat. No. 11,006,981 B2 describes a method of manufacturing a surgical implant that includes simultaneously forming a first component and a second component of the surgical implant. The surgical implant is designed to be manufactured via methods of additive manufacturing, i.e., layer-by-layer techniques. A first component of the surgical implant may have a hollow interior portion and at least one opening, and a second component may have a head portion disposed within the hollow interior portion and a shaft portion extending through the at least one opening, wherein the head portion is configured and dimensioned to be larger than the at least one opening and therefore unable to pass therethrough. By means of this, a polyaxial implant can be provided.

SUMMARY

It is an object of the invention to provide a coupling device for coupling a bone anchoring element to a rod, in particular in a polyaxial manner, where the coupling device is improved and/or is an alternative compared to conventional coupling devices, and methods of manufacturing and using such a coupling device.

According to an aspect of the invention, the coupling device includes a receiving part having a head receiving portion for receiving a head of the bone anchoring element and a rod receiving portion for receiving the rod, and a locking member movable relative to the receiving part between a first position in which the head is insertable into the head receiving portion and a second position in which the head is prevented from being removed from the head receiving portion, wherein the receiving part and the locking member are inseparably interconnected with each other.

The receiving part and the locking member are interconnected parts which are movable relative to each other, but are inseparable prior to using the coupling device and/or during use. In other words, under conditions of use prior or during surgery and in the implanted state, the receiving part and the locking member cannot be separated from each other without damaging or destroying the coupling device (e.g., without plastically or otherwise permanently deforming or damaging at least one of the receiving part or the locking member). Hence, the coupling device is free from any separate fixation members that would otherwise keep the receiving part and the locking member together. Compared to conventionally produced coupling devices, the coupling device according to embodiments of the invention may therefore include less parts. In addition, the parts are more safely secured together.

In particular, the coupling device according to embodiments of the invention may be made using an additive manufacturing method, more specifically, an additive layer manufacturing method. In such a method, the coupling device is built up by layer-wise deposition of a building material, and solidifying or melting the material in each layer at the cross-section of the coupling device in the respective layer. A suitable method is, for example, selective laser sintering (SLS) or selective laser melting (SLM), in which the building material is a powder, such as a metal powder or a plastic powder, and a laser is used to melt the powder. Alternatively, an electron beam may be used to melt the building material. Also, other known methods of powder based three-dimensional printing in which layers of a powder material are deposited and solidified by applying a binder material at positions corresponding to the coupling device may be used. Still further additive manufacturing methods, for example, fused deposition modeling (FDM) may also be applied.

Hence, since it is possible to produce almost any shape with an additive manufacturing method, the receiving part and the locking member may have complex shapes and/or may be interconnected in a manner that may be difficult or impossible to manufacture conventionally. Thereby, an improvement with regard to the strength of the parts and an improved transfer of forces may be achieved.

In a particular embodiment, the receiving part and the locking member can be built up as a monolithic unit. The receiving part and the locking member may be separated after they have been manufactured with the additive manufacturing method. More specifically, the monolithic unit may include a holding portion that facilitates holding of the monolithic unit with a tool to allow separation of the receiving part and the locking member from the holding portion by cutting. This allows to precisely separate the receiving part and the locking member at respective positions suitable for permitting the locking member to move relative to the receiving part after the separation step. As a result of the separation, the receiving part and the locking member form an integrated unit.

It shall be noted that the additive manufacturing method, in particular, the additive layer manufacturing method, influences the appearance of the coupling device. For example, the layers may be visible on the surface of a particular finished object, even if the integrated unit including the receiving part and the locking member is post-treated, such as polished, etched, coated or otherwise treated. It may also be possible to identify traces of the laser or electron beam when inspecting the fabricated object. Hence, the additive manufacturing method, in particular the additive layer manufacturing method, can be distinguished on the basis of finished object compared to a conventional subtractive manufacturing method.

In a particular embodiment, the coupling device is configured to provide a bottom-loading polyaxial bone anchoring device which allows insertion of the head of the bone anchoring element from the bottom end of the coupling device. Alternatively, the coupling device may be designed for a top-loading polyaxial bone anchoring device in which the bone anchoring element is inserted from the top end of the receiving part into the coupling device.

A polyaxial bone anchoring device according to embodiments of the invention includes, in addition to the coupling device, a bone anchoring element having a head and a shank, preferably wherein the head has a spherically-shaped outer surface portion.

BRIEF DESCRIPTION OF THE DRAWINGS

Further features and advantages of the invention will become apparent from the description of embodiments by means of the accompanying drawings. In the drawings:

FIG. 4 shows a perspective view from a top of the coupling device of the bone anchoring device shown in FIGS. 1 to 3.

FIG. 5 shows a perspective view from a bottom of the coupling device of FIG. 4.

FIG. 6a shows a cross-sectional view of the coupling device of FIGS. 4 and 5, the cross-section taken in a plane extending through centers of legs of a receiving part of the coupling device and perpendicular to a longitudinal axis of a rod channel of the receiving part.

FIG. 6b shows an enlarged view of a detail of FIG. 6a.

FIGS. 12a to 12f show perspective views of steps of moving the locking member relative to the receiving part of the coupling device according to the first embodiment with an instrument, and inserting and fixing the rod.

FIG. 21 shows a perspective view from a bottom of the coupling device according to the third embodiment, wherein the receiving part and a locking member of the coupling device are in a first position relative to each other.

FIG. 22 shows a perspective view of the coupling device of FIG. 21, wherein the receiving part and the locking member are in a second position relative to each other.

FIG. 23 shows a cross-sectional view of the coupling device of FIG. 21, wherein the cross-section is taken in a plane including a central axis of the coupling device and arranged at an angle with respect to a longitudinal axis of a rod channel of the receiving part.

FIG. 24 shows a cross-sectional view of the coupling device of FIG. 22, wherein the cross-section taken in a plane extending perpendicular to the longitudinal axis of the rod channel and extending through centers of the legs of the receiving part.

DETAILED DESCRIPTION

Figure 1:
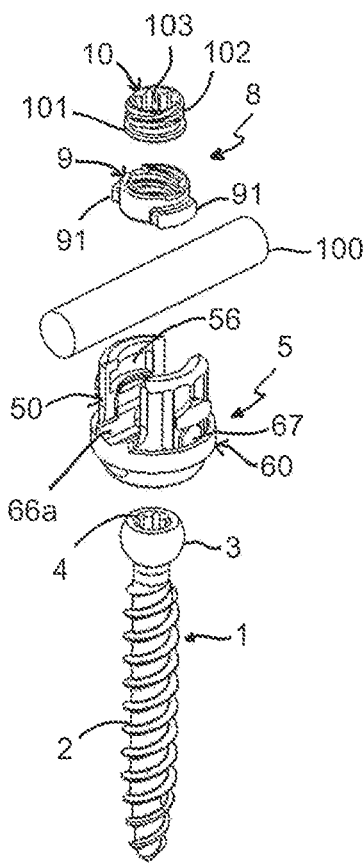
FIG. 1 shows a perspective exploded view of a first embodiment of a polyaxial bone anchoring device including a first embodiment of a coupling device.
Figure 2:
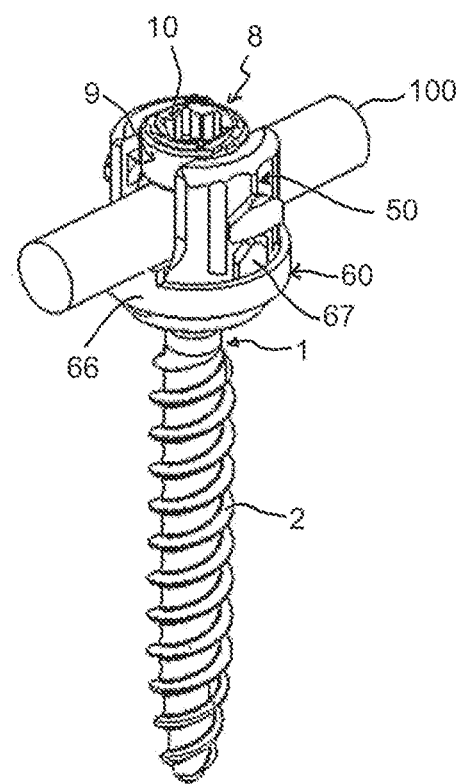
FIG. 2 shows a perspective view of the polyaxial bone anchoring device of FIG. 1 in an assembled state.
Figure 3:
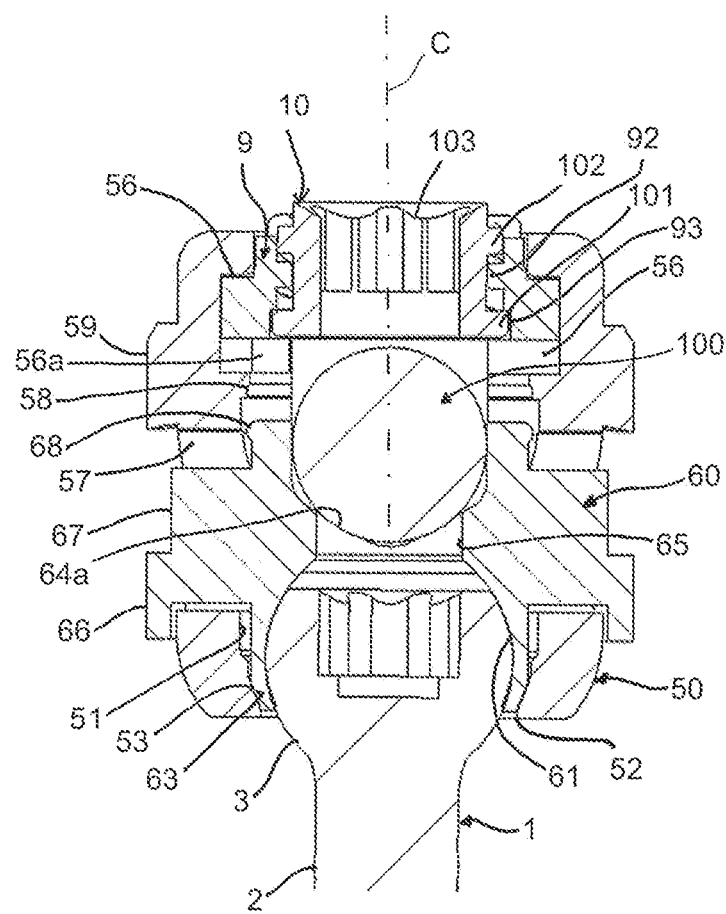
FIG. 3 shows a cross-sectional view of the polyaxial bone anchoring device of FIGS. 1 and 2, wherein the cross-section is taken in a plane extending perpendicular to a longitudinal axis of an inserted rod and through centers of legs of the coupling device.
Figure 7:
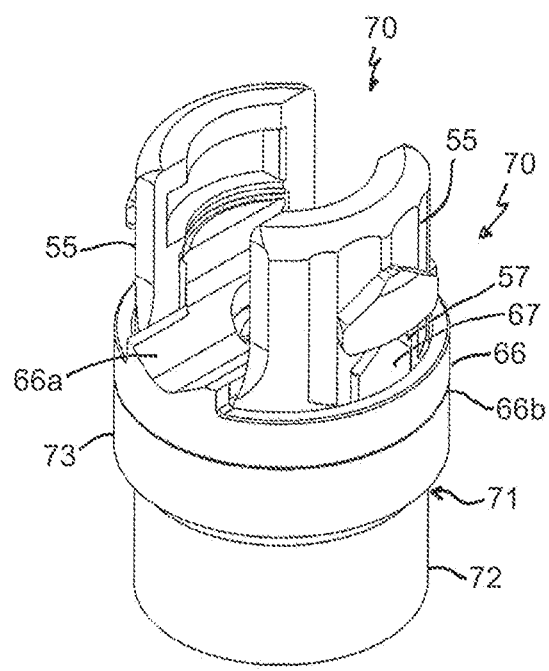
FIG. 7 shows a perspective view from a top of a monolithic unit including the receiving part and a locking member of the coupling device of FIGS. 4 to 6b and a holding portion for holding the monolithic unit.

A polyaxial bone anchoring device according to a first embodiment is shown in FIGS. 1 to 3. The bone anchoring device includes a bone anchoring element 1 having a shank 2 with a threaded portion and a head 3. The head 3 has a spherically-shaped outer surface portion and, on its side opposite to the shank 2, a recess 4 for engagement with a tool. A coupling device 5 according to a first embodiment is provided for coupling the bone anchoring element 1 to a rod 100. The polyaxial bone anchoring device further includes a fixation assembly 8 having a first member 9 and a second member 10 configured to be coupled to the first member 9.

Referring in addition to FIGS. 4 to 6b, the coupling device 5 includes a receiving part 50 and a locking member 60 that are separate parts which are interconnected with each other. In greater detail, the receiving part 50 and the locking member 60 are interconnected in a manner such that they are movable relative to each other but cannot be separated from each other. More specifically, the receiving part 50 and the locking member 60 cannot be separated from each other without damaging or destroying the coupling device 5. Hence, the coupling device 5 forms an integrated unit including the receiving part 50 and the locking member 60. In this embodiment, the receiving part and the locking member is each a monolithic part.

The receiving part 50 has a first end or top end 5a and an opposite second end or bottom end 5b, and is substantially cylindrical with a longitudinal axis C extending through the top end 5a and the bottom end 5b. A coaxial passage 51 is formed in the receiving part 50 that extends from the top end 5a to the bottom end 5b where the passage defines an opening 52. The passage narrows towards the opening 52, for example, with a conically-shaped section 53 that is configured to cooperate with a portion of the locking member 60, as described in greater detail below. The width or diameter of the opening 52 is greater than a greatest width of the head 3 of the bone anchoring element 1. This permits insertion of the head 3 from the bottom end 5b into the receiving part 50. Further, the receiving part 50 defines a recess 54 starting at the top end 5a and extending in the direction of the bottom end 5b. By means of the recess 54, two free legs 55 are formed that are open towards the top end 5a and that define a channel for receiving the rod 100. A bottom of the recess 54 is configured to receive a portion of the locking member 60 therein and provides space for the locking member 60 to move in an axial direction. At a distance from the top end 5a, the passage 51 widens into a circumferentially extending recess 56 on each of the legs 55 that serve for receiving radially protruding wings 91 of the first member 9 of the locking assembly 8 therein. At one end of each of the circumferential recesses 56, an abutment 56a is formed that prevents the wings 91 from moving out of the recess 56, as explained in greater detail below. At the opposite end, the recess 56 is open towards the rod channel. It shall be noted that such an abutment 56a is formed at the end of each of the recesses in a specific circumferential direction such that when the first member 9 is inserted and rotated in this direction, in the clockwise direction in the example shown, the circumferentially leading end of each wing 91 abuts in the respective recess 56 against the corresponding abutment 56a. The height of the circumferential recesses 56 is greater than an axial height of the wings 91 to facilitate the insertion of the fixation assembly.

At the center of each of the legs 55 at a distance from the top end 5a, a recess 57 is formed that extends fully through the receiving part 50 from the outside to the passage 51 to permit a portion of the locking member 60 to extend therethrough. The recesses 57 may have a substantially pentagonal or house-like contour, with a roof portion having a top oriented towards the first end 5a of the receiving part 50. An axial height of the recesses 57 is such that a corresponding portion of the locking member 60 can move to some extent therein in the axial direction.

The passage 51 can have various portions, and does not need to have a constant inner diameter. Specifically, between the recesses 57 and the recesses 56, the passage 51 has a reduced diameter section with a groove 58, preferably with a rounded cross-section, for example a spherical segment-shaped cross-section, at a lowermost position of the reduced diameter section. The groove 58 serves for receiving a portion of the locking member 60 when the locking member 60 is at an insertion position.

Moreover, the receiving part 50 includes a tool engagement protrusion 59 on each of the legs 55 at a center thereof in the circumferential direction and above the recesses 57. For example, the tool engagement protrusions 59 may have a roof-shaped upper side 59a.

The locking member 60 has a top end 6a and an opposite bottom end 6b. The bottom end 6b is configured to face the opening 52 in the receiving part 50. Between the top end 6a and the bottom end 6b, the locking member 60 has a shape that is substantially cylindrical, except for the portions that are configured to extend out of the passage 51 of the receiving part 50. An outer width of the cylindrical portion of locking member 60 is smaller than the inner width of the passage 51, so that the locking member 60 can move to some extent within the passage 51. Adjacent to the bottom end 6b, a hollow interior head receiving section 61 is formed that provides a seat for the head 3 of the bone anchoring element 1. The head receiving section 61 has a shape and in particular an inner diameter that is adapted to the outer diameter of the head 3 of the bone anchoring element 1. In particular, the head receiving section 61 is configured to extend over a section of the head 3 with a greatest diameter. An opening is defined at the bottom end 6b through which the head 3 of the bone anchoring element 1 can enter into the head receiving section 61. In particular, the head receiving section 61 is flexible and can expand when the head 3 is inserted. Moreover, the head receiving section 61 is configured to be compressed by an external force to clamp and finally lock the head 3 in the head receiving section 61. To achieve the flexibility, a plurality of slits 62 that are open towards the second end 6b may be provided. An end portion 62a of each the slits may be enlarged. Various shapes may be used for the end portion 62a, such as a circular or a rounded triangular shape, or any other shape that achieves a suitable flexibility.

Figure 9:
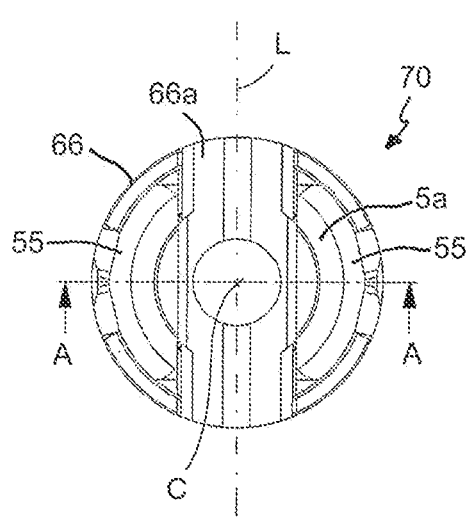
FIG. 9 shows a top view of the monolithic unit of FIGS. 7 and 8.
Figure 10:
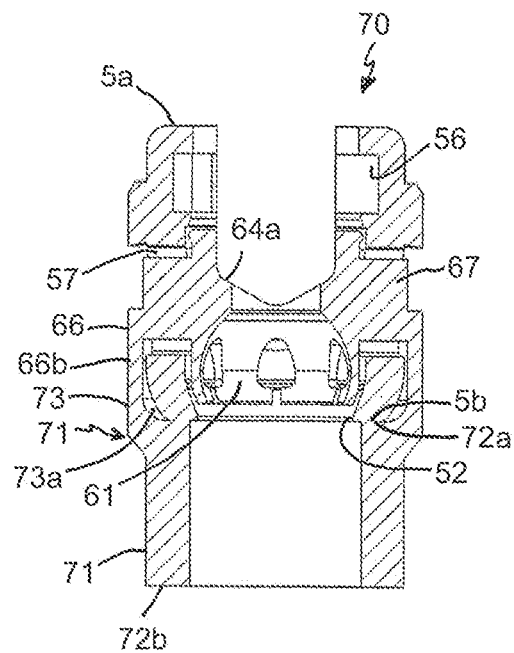
FIG. 10 shows a cross-sectional view of the monolithic unit of FIGS. 7 to 9, the cross-section taken in a plane along line A-A in FIG. 9.

Adjacent to the bottom end 6b, the outer surface of the locking member 60 has a narrowing portion 63, in the example, a conically tapering portion 63 that is configured to cooperate with the narrowing portion 53 of the receiving part 50. When the narrowing portions 53, 63 of the receiving part 50 and the locking member 60, respectively, cooperate, an inwardly directed force is generated that compresses the head receiving section 61. Adjacent to the top end 6a, a recess 64 is provided that has substantially flat and substantially parallel sidewalls and, as seen in the cross-sectional views of FIGS. 3 and 6a, a substantially V-shaped bottom that provides a rod support surface 64a. The recess 64 is aligned with the recess 54 of the receiving part 50 and defines a channel axis L of the rod channel (see FIG. 9) that is perpendicular to the central axis C.

A coaxial bore 65 extends from the bottom of the recess 64 into the head receiving section 61. The coaxial bore 65 facilitates access with a tool, such as a screwdriver, to engage the recess 4 in the head 3 of the bone anchoring element 1.

The locking member 60 further includes a ring portion 66 that extends completely around the receiving part 50 and that is monolithic with the cylindrical portion of the locking member 60. In greater detail, the ring portion 66 is monolithically connected to the cylindrical portion of the locking member 60 via protrusions 67 which are offset by 180° from one another and that extend through the recesses 57, respectively. The shape of the protrusions 67 is substantially pentagonal and house-like shaped with a roof portion oriented towards the top end 6a. In the axial direction, the height of the protrusions 67 is smaller than the height of the recesses 57, so that the locking member 60 can move in the axial direction by a distance limited by the upper and lower ends of the recesses 57. The ring portion 66 is also monolithically connected to the inner cylindrical portion of the locking member 60 by elevated portions 66a that are offset by 180° from one another and that form extensions of the rod support surface 64a. By means of this, the rod support surface is prolonged and extends to the outside of the receiving part 50.

The ring portion 66 extends from a lower region of the protrusions 67 radially outward and downward in the direction of the lower end 5b of the receiving part 50. An inner diameter of the ring portion 66 is slightly greater than an outer diameter of the receiving part in the region below the recesses 57, so that the ring portion can move downward. To facilitate the movement of the ring portion 66, the receiving part 50 may have flattened outer surface portions 500 at positions corresponding to the circumferential positions of the elevations 66a. An outer diameter of the ring portion 66 may be the same or only slightly greater than an outer diameter of the receiving part 50 in the regions of the tool engagement protrusions 59.

Adjacent to the top end 6a, the locking member 60 include a circumferential protrusion 68 with a rounded shape that is configured to enter into the rounded groove 58 in the receiving part 50 to prevent upward movement of the locking member 60 when the locking member is at an insertion position in which the head 3 can be inserted into the head receiving section 61.

The locking member 60 is configured to assume a first position relative to the receiving part in which the head 3 can enter through the lower opening 52 of the receiving part into the head receiving section 61 of the locking member 60. Furthermore, the locking member 60 can assume at least a second position in which the locking member 60 is moved closer to the bottom end 5b of the receiving part 50 so that the narrowing portions 63 of the locking member 60 and the narrowing portion 53 of the receiving part engage and an inserted head 3 is prevented from being removed from the opening 52. Moreover, in the second position, the head 3 may be clamped or finally locked in the receiving part 50. As shown in the figures, the locking member 60 and the receiving part 50 cannot be disassembled from each other.

An embodiment of a method of manufacturing the coupling device will be described, with reference to FIGS. 7 to 10. A preferred manufacturing method is an additive layer manufacturing method, whose principles are well-known in the art. The coupling device is produced consecutively from layers which correspond to the cross-section of the coupling device in the respective layer. As an example, a powder bed based layer manufacturing technique, such as selective laser melting (SLM), includes the steps of applying a layer of building material, such as a powder, in particular a metal powder or a plastic powder, onto a support surface, and selectively solidifying or melting the powder at positions corresponding to the cross-section of the coupling device in the respective layer. Subsequently, the steps of applying and melting further layers of the coupling device are repeated until the coupling device is finished. The data of the cross-section of the coupling device in the respective layer and the data for controlling the layer manufacturing apparatus result from CAD or CAM data of the coupling device and corresponding slice data.

Figure 8:
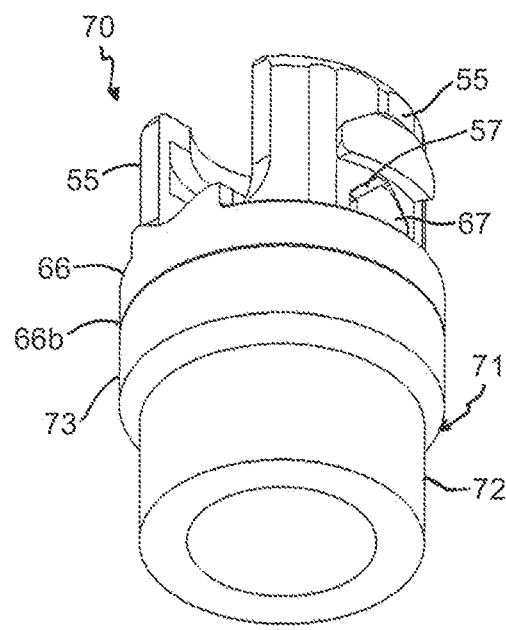
FIG. 8 shows a perspective view from a bottom of the monolithic unit of FIG. 7.

The receiving part 50 and the locking member 60 are manufactured as a monolithic unit 70, for example, by using such an additive layer manufacturing technique. The monolithic unit 70 is shown in FIGS. 7 to 10 and includes a holding portion 71 that is monolithically connected with the locking member 60 and also with the receiving part 50. In the example shown, the holding portion 71 includes a first tube-shaped portion 72 with an upper end 72a and a lower end 72b. The upper end 72a is adjacent to the lower end 5b of the receiving part 50. At the upper end 72a or close thereto, a second tube-shaped portion 73 extends upwards that surrounds the lower end of the receiving part 50 with a gap 73a therebetween and that is monolithically connected with the ring portion 66 of the locking element 60. After building up, the monolithic unit 70 is held at the first tube-shaped portion 72 in a machine, and is cut at the two predetermined cutting positions where the holding portion 71 is connected to the receiving part 50 and the locking member 60, respectively. The first cutting position is the top end 72a of the first tube portion 72 and the second cutting position 66b is the intended lower end of the ring portion 66 as shown in FIG. 8.

The predetermined cutting positions 72a, 66b may be marked, for example, through externally visible markings that are generated during the layer-wise build up. For example, the cutting positions may be indicated by a surface structure and/or may have a structure that facilitates cutting, such as a weakened structure, for example, a perforated structure or a structure that is less solidified, such that the separation after building is more easily facilitated at the respective positions. When the monolithic unit 70 has been built up, unmelted or unsolidified building material can be removed through the openings which are present in the monolithic unit.

Once separated, the receiving part 50 and the locking member 60 which form an integrated unit, may be further treated, for example, polished, sand-blasted, etched, or coated. However, in some cases no after-treatment is carried out, since a rough surface that may result from the building process may be desirable in some applications.

Referring again to FIGS. 1 to 3, the first member 9 of the fixation assembly 8 is substantially cylindrical and fits into the passage 51 of the receiving part 50. Two wings 91 are located at opposite sides of the first member 9 and are dimensioned such that they are configured to engage the circumferential recesses 56 in the receiving part 50. Further, the first member 9 defines a passage 92 from a top end to a bottom end, where the inner wall preferably has a small number of thread turns 94, preferably only one to three turns for threaded cooperation with the second member 10. Adjacent to the lower end of the first member 9, a recess 93 is formed for receiving an annular projection of the second member 10 that prevents the second member 10 from being removed when the fixation assembly is in use. The thread may be, for example, a flat thread or square thread. Hence, the threaded connection between the first member 9 and the second member 10 is more easy to manufacture, in particular, when an additive layer manufacturing technique is used. The second member 10 is configured to be arranged in the passage 92. The second member includes an annular projection 101 at its lower end that is configured to be received in the recess 93 of the first member and to abut against the step 93a formed by the recess 93. Furthermore, the second member 10 includes an outer thread 102 for cooperating with the thread 94 of the first member 9. At a side opposite to the annular projection 101, the second member 10 has a tool engagement recess 103.

When the first member 9 and the second member 10 are together and the annular projection 101 abuts against the step 93a, the lower sides of the first member and the second member may be flush with each other. The first member 9 and the second member 10 may be manufactured together, preferably with an additive layer manufacturing technique similarly as described in connection with the coupling device 5. The two members may be manufactured such that they are preliminarily held together by a clamping force, or they may be manufactured as a monolithic unit with a defined breaking section that permits breaking of the connection between the two members when they are moved relative to each other.

The material of the polyaxial bone anchoring device, and in particular of the coupling device and the fixation assembly, may be preferably a body-compatible metal or metal alloy or a body-compatible plastic material. Such a material can be, for example, stainless steel or titanium or, in the case of a plastic material, polyether ether ketone (PEEK). Such materials are available in powder form for use in the additive layer manufacturing method as described above.

Figures 11A, 11B, 11C, 11D:
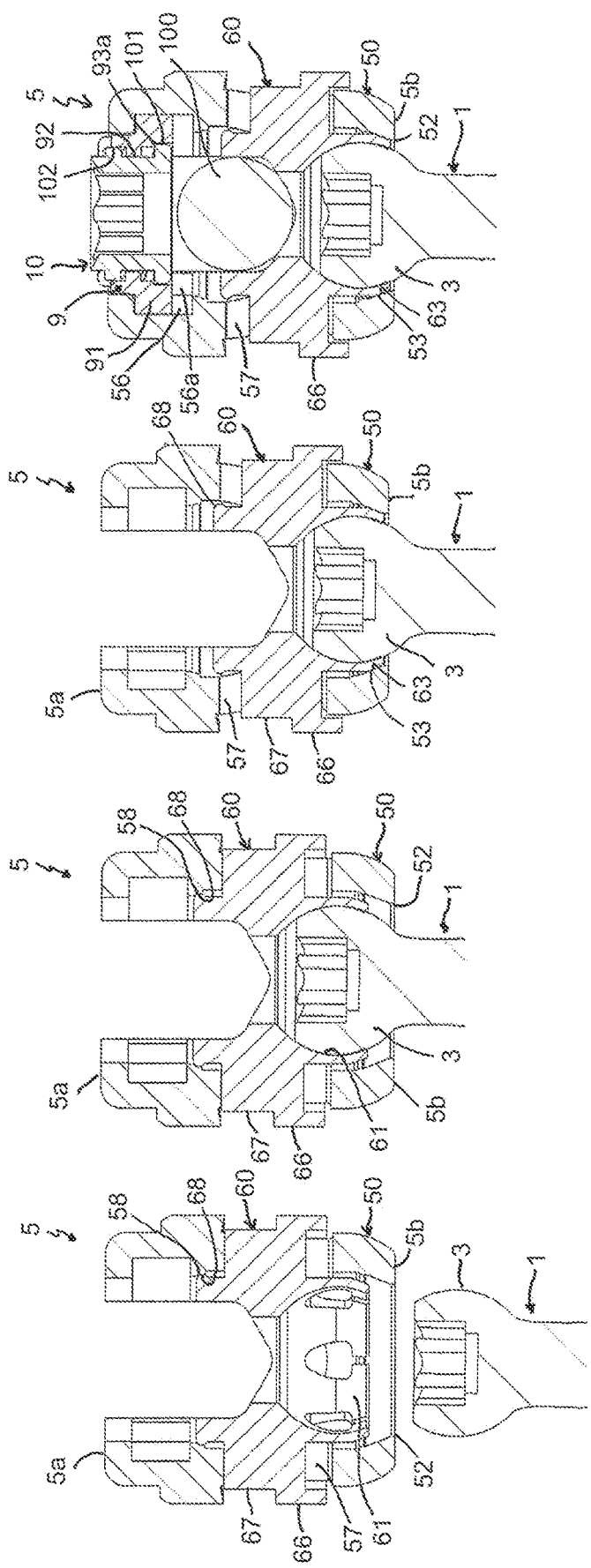
FIG. 11a to FIG. 11d show cross-sectional views of steps of assembling the polyaxial bone anchoring device according to the first embodiment.
Figure 13:
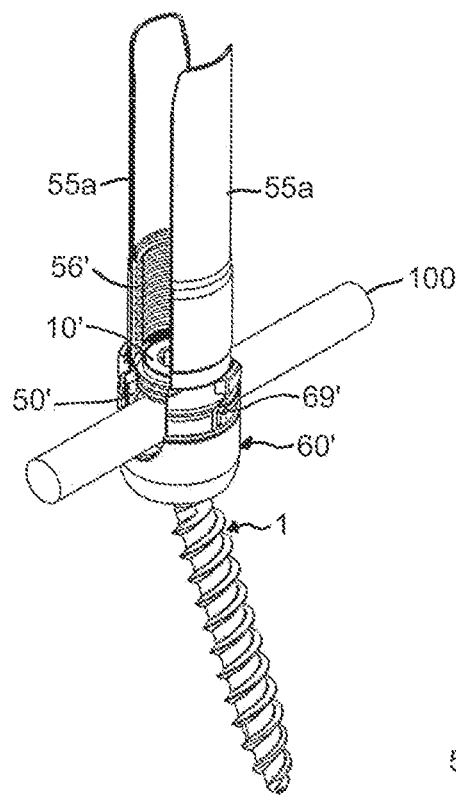
FIG. 13 shows a perspective view of a second embodiment of the polyaxial bone anchoring device with a second embodiment of the coupling device in an assembled state.

Steps for assembling the polyaxial bone anchoring device of FIGS. 1 to 10 will be described, with reference to FIGS. 11a and 11d. In a first step as shown in FIG. 11a, the locking member 60 is in the first position which is the insertion position. The rounded protrusion 68 engages the rounded groove 58 and the head receiving section 61 is in the passage 51 at a position where the head receiving section can expand when the head 3 is inserted. The head 3 of the bone anchoring element 1 is moved towards the opening 52 of the receiving part 50. Next, as shown in FIG. 11b, the head 3 is inserted through the opening 52 into the head receiving section 61 of the locking member 60. Since the locking member 60 abuts against the upper portion of the groove 58 and/or against the upper portion of the recesses 57, a further upward movement of the locking member 60 relative to the receiving part 50 is hindered.

As depicted in FIG. 11c, the locking member 60 is then moved downward towards the second end 5b of the receiving part 50 until the respective narrowing portions 53, 63 of the receiving part and of the locking member engage. This is the second position of the locking member relative to the receiving part 50. Since the lower opening 52 is narrowed or otherwise partially blocked by the presence of the compressed head receiving section 61 of the locking member, the head 3 cannot be removed through the opening 52 when the locking member is at the second position. It shall be noted that the head 3 may also be frictionally held in the head receiving section 61 in the second position. This permits the bone anchoring element 1 to be held temporarily at a particular angular position relative to the coupling device without finally locking the head 3.

Next, as shown in FIG. 11d, the rod 100 is inserted into the rod channel until the rod rests on the rod supporting surface 64a of the locking member 60. Due to the V-shaped contour of the rod supporting surface 64a, it is possible to safely support rods of different diameters thereon. Finally, the locking assembly 8 is inserted between the legs 55 of the receiving part 50. This can be achieved by orienting the first member 9 such that the wings 91 enter the rod channel. Then, the locking assembly 8 is rotated so that the wings 91 engage the recesses 56 until they abut against the abutment 56a. For fixation of the rod 100, the second member 10 is screwed downward until its lower surface abuts against the rod and fixes the rod. During this step, the rod is also moved further downward and presses the locking member 60 deeper into the narrowing portion 53 of the receiving part 50 to finally lock the head 3 in the coupling device.

In clinical use, usually two or more polyaxial bone anchoring devices are connected to the rod 100. In a first way of use, the bone anchoring element 1 is first inserted into bone, for example, into a pedicle of a vertebra, and the coupling device 5 is mounted on the head 3 of the bone anchoring element 1 thereafter. In a second alternative way of use, the bone anchoring element 1 and the coupling device 5 are pre-assembled and inserted in the preassembled condition into the bone, for example, into the pedicles of adjacent vertebrae.

Referring to FIGS. 12a to 12c, steps of operating the polyaxial bone anchoring device will be explained. As depicted in the figures, a front portion of an instrument 200 includes a pair of elongate first and second instrument sections 201, 202 having free ends 201a, 202a, wherein the pair is separated by a recess 203. It shall be noted that the central first instrument section 201 may be sandwiched between two second instrument sections 202 arranged to the left and to the right thereof. The width of the recess 203 allows the rod 100, and more specifically the elevations 66a of the locking member 60, to pass therethrough. The second instrument sections 202 may be connected at some distance from their free ends by a bridge 204. Further parts of the instrument 200 include a mechanism for moving the second sections 202 relative to the first sections 201. Each of the first sections 201 defines, at a distance from the free end 201a, a recess 201b that is shaped and sized so as to engage the tool engagement protrusions 59 at the receiving part 50. The second sections 202 face the other corresponding second sections 202 on the opposite side of the recess 203.

Moreover, the second sections 202 can be axially displaced with respect to the first sections 201. With the instrument 200, it is possible to move the locking member 60 relative to the receiving part 50 from the first position to the second position. In greater detail, as shown in FIG. 12*a*, the instrument is oriented relative to the coupling device such that the recess 203 and the rod channel are aligned. Then the instrument is moved downward to engage the protrusions 59. The bridge 204 may render the pair of instrument sections slightly flexible or otherwise able to spread apart with respect to each other, such that the front portion can be placed over the receiving part and such that the protrusions 59 snap into the recesses 201*b*. The free ends 201*a* and 202*a* are resting on the upper surface of the ring portion 66 of the locking member 60 or are slightly above it. As further depicted in FIG. 12*c*, the second sections 202 are then moved downwards and press onto the upper surface of the ring portion 66 to move the locking member 60 downwards and deeper into the narrowing portion 53 of the receiving part 50. By means of this, the head 3 can be preliminarily held or even locked without the rod being in the rod channel. In other words, the rod channel can remain unobstructed. This permits performing of correction steps independent of use of the rod and/or where the rod will not get in the way of or otherwise hinder performing of any of the correction steps. Next, as shown in FIGS. 12*d* and 12*e*, the rod 100 is inserted and moved down onto the rod support 66*a* with a pushing member 205 that is movable between the pair of instrument sections. Finally, the fixation assembly 8 is inserted and tightened to fix the rod, as shown in FIG. 12*f*.

Referring to FIGS. 13 to 18, a second embodiment of the polyaxial bone anchoring device with a second embodiment of the coupling device will be described. Parts and portions that are identical or similar to the first embodiment have the same reference numerals, and the descriptions thereof will not be repeated. The coupling device 5' includes a receiving part 50' and a locking member 60'. The receiving part 50' is substantially cylindrical and defines a passage that extends fully from the top end 5*a* to the bottom end 5*b*, and a recess 54' at the top end 5*a*, by means of which two legs 55' are formed and which define the rod channel. The legs 55' include extensions 55*a* that prolong the legs 55' above the top end 5*a* of the receiving part 50'. The extensions 55*a* may be broken off later at a weakened breaking section 55*b*. Such extensions may be useful in minimally invasive surgery (MIS) for guiding instruments and/or other parts to the implantation site beneath the skin of a patient. An internal thread 56' may be provided which extends from a portion of the extensions 55*a* into the passage below the top end 5*a*. In this embodiment, a fixation member 8' in the form of a set-screw is used that cooperates with the internal thread 56'. A lower portion 501 (FIG. 18) of the receiving part 50' adjacent to the bottom end 5*b* has a reduced outer diameter and a reduced wall thickness in a region where a seat for the head 3 is provided, so that a portion of the locking member 60' can extend into the space resulting from the reduction of the outer diameter of the lower portion.

Figure 14:
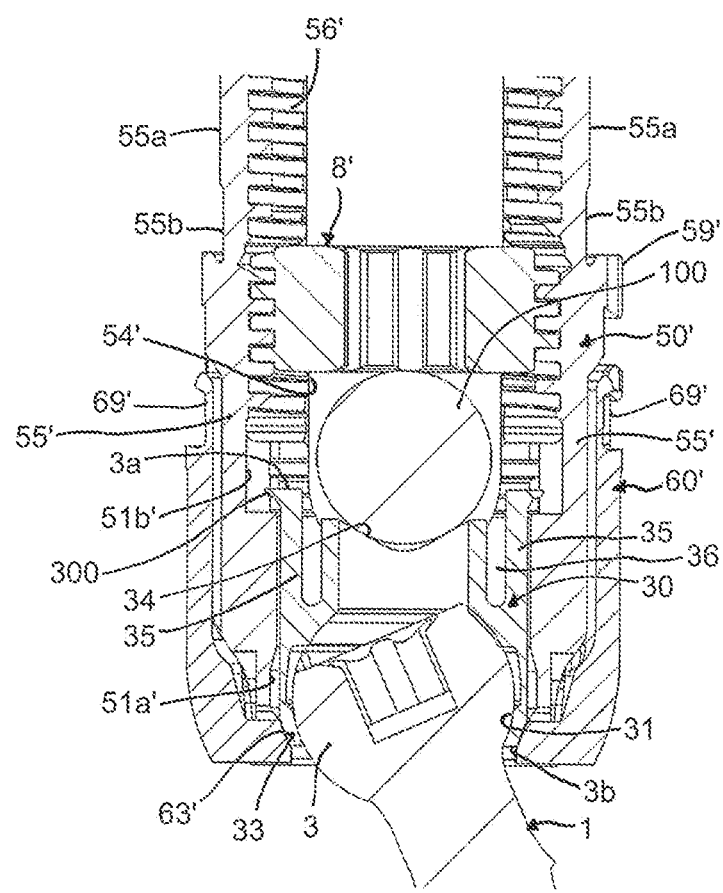
FIG. 14 shows a cross-sectional view of a portion of the polyaxial bone anchoring device of FIG. 13, the cross-section taken in a plane extending perpendicular to a longitudinal axis of an inserted rod and extending through center of legs of a receiving part of the coupling device.
Figure 16:
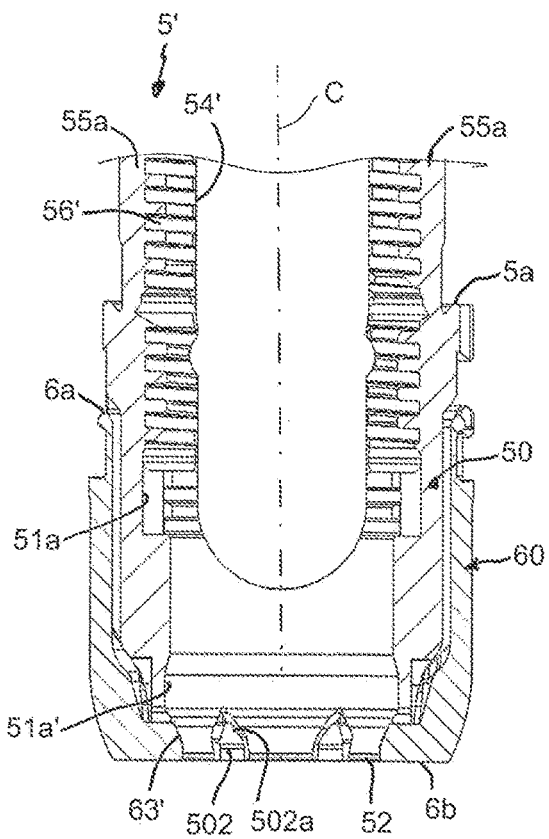
FIG. 16 shows a cross-sectional view of an integrated unit that forms the coupling device according to the second embodiment, in a state separated from the holding portion shown in FIG. 15.
Figure 18:
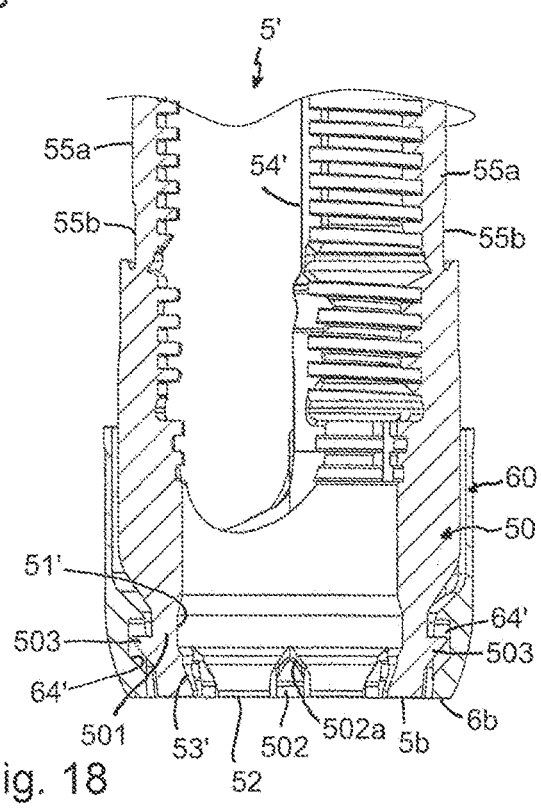
FIG. 18 shows a cross-sectional view of the coupling device of FIGS. 16 and 17, the cross-section taken in a plane along line B-B in FIG. 17.
Figure 19:
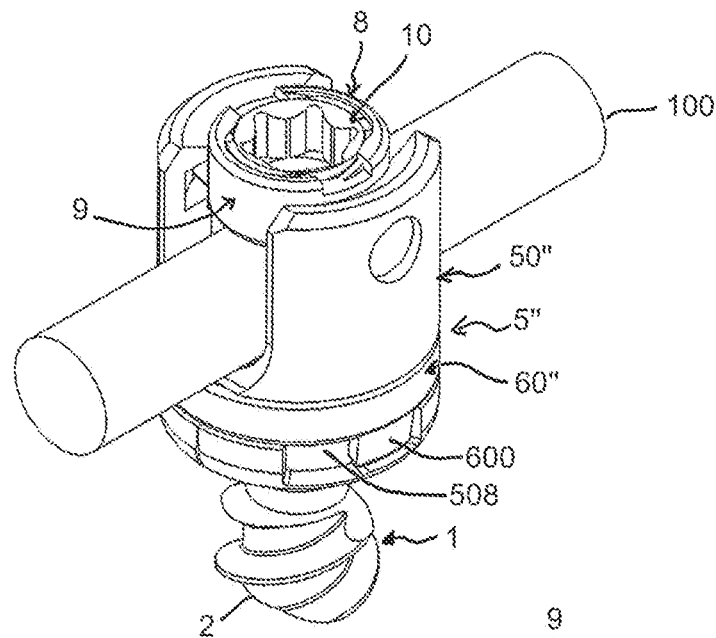
FIG. 19 shows a perspective view of a third embodiment of the polyaxial bone anchoring device with a third embodiment of the coupling device in an assembled state.

Referring in particular to FIGS. 14, 16 and 18, the lower portion of the receiving part 50' adjacent to the bottom end 5*b* includes an inner narrowing portion 53' and a plurality of recesses 502 that are open towards the lower end 5*b* and extend to a distance from the lower end 5*b*. The end portion 502*a* of the recesses 502 may have a triangular or roof-shaped contour. The recesses 502 serve for permitting a portion of the locking member 60' to pass therethrough. In the passage, an enlarged accommodation space 51*a*' is formed that extends above the narrowing portion 53' to a distance from the second 5*b* and that is configured to receive an expandable head receiving portion of a separate pressure member 30 therein.

In addition, as can be seen in particular in FIG. 18, the receiving part 50' includes a plurality of projections 503 on its outer surface that may each have a lower inclined and an upper flat surface and that are configured and shaped to be accommodated in corresponding recesses at an inner wall of the locking member 60'. The projections 503 may be arranged at distances from each other around the circumference of the outer surface of the lower portion 501 of the receiving part 50'. Furthermore, tool engagement protrusions 59' may also be formed at an outer surface of the legs 55' that may be asymmetrically arranged with respect to the rod channel, as can be seen in FIG. 14.

As shown in FIG. 14, the separate pressure member 30 has a top end 3*a* and a bottom end 3*b*, and is arranged in the passage of the receiving part 50' such that the bottom end 3*b* faces towards the bottom end 5*b* of the receiving part 50'. Adjacent to the bottom end 3*b*, the pressure member 30 includes a head receiving portion 31 to receive the head 3 of the bone anchoring element 1 therein. The head receiving portion 31 may be flexible, wherein the flexibility may be achieved by one or more slits that extend from the bottom end 3*b* to a distance thereof. The outer surface portion 33 adjacent to the bottom end 3*b* of the separate pressure member 30 narrows towards the bottom end 3*b*, and is configured to cooperate with the narrowing portion 53' of the receiving part 50' and with a portion of the locking member 60'. The pressure member 30 further includes at a distance from the head receiving portion 31 a rod support surface 34 that may have a substantially V-shaped contour and that is aligned with the rod channel when the pressure member is mounted or otherwise assembled to the receiving part. To the left and to the right of the rod support surface 34, when viewed in a longitudinal direction of the rod support surface 34, two arms 35 are provided that are separated from the rod support surface by grooves 36. The end portion of the arms 35 at the top end 3*a* of the pressure member 30 have an outward projection 300 that extends into an enlarged section 51*b*' of the passage of the receiving part 50'. The arms 35 may be slightly flexible and may be compressed towards the central longitudinal axis C of the receiving part 50' when the separate pressure member 30 is inserted from the free end of the legs 55' into the receiving part 50'.

The separate pressure member 30 can assume in the receiving part 50' at least a first position in which the head receiving portion 31 is expandable so that a head 3 can be inserted, and a second position in which the head receiving portion 31 is at a lower position so that the narrowing outer surface portion 33 engages the narrowing inner surface portion 53' of the receiving part 50'. In the first position, the pressure member 30 may be secured against moving upward by the outward projection 300 of the arms 35 abutting against an upper end of the enlarged section 51*b*' when the head 3 is inserted.

The locking member 60' forms a ring, or more specifically, forms a sleeve that extends around the receiving part 50'. The top end 6*a* of the locking member 60' extends up to a distance from the top end 5*a* of the receiving part 50'. At the bottom end 6*b*, the locking member 60' includes inwardly directed projections 63' at positions that correspond to the recesses 502 in the receiving part 50'. The projections 63' are configured to enter into the recesses 502 at the lower end of the receiving part 50'. In particular, the projections 63' may have an inner surface that narrows towards the lower end 6*b* of the locking member 60', preferably an inner surface that narrows conically at a same or similar angle as the outer surface 33 of the pressure member 30.

Furthermore, in the inner wall of the locking member 60', recesses 64' are formed at positions corresponding to the projections 503 of the receiving part 50' and are configured to accommodate the projections 503 and enable a limited movement of the locking member 60' in the axial direction relative to the receiving part 50'. The flat upper surfaces of the projections 503 abut against the edges of the recesses 64', respectively, so that the locking member cannot fall off or otherwise detach from the receiving part. In an upward direction, the locking member 60' would abut against the ends of the recesses 502. Hence, the receiving part 50' and the locking member 60' form an integrated unit and cannot be separated from each other without damaging or destroying the respective parts. Lastly, at a distance from the top end 6a, the locking member 60' includes at least one, preferably two opposite tool engagement portions 69' for engagement with a tool.

It shall be noted that the seat for the head 3 is provided in the head receiving portion 31 of the pressure member 30. Hence, in this embodiment, the receiving part 50' and the pressure member 30, as well as the portions 63' of the locking member 60', together provide the seat for the head 3.

Figure 15:
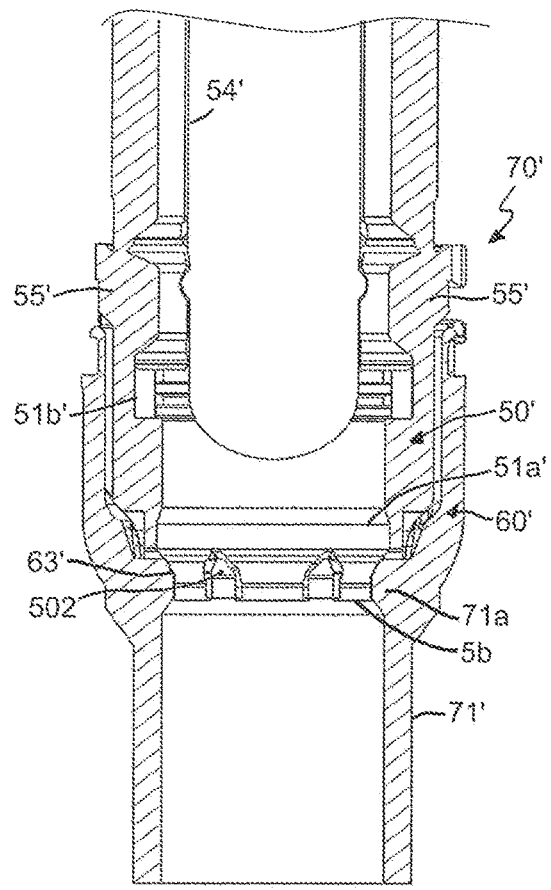
FIG. 15 shows a cross-sectional view of a monolithic unit of the coupling device according to the second embodiment of FIGS. 13 and 14, further including a holding portion, wherein the cross-section is taken in a plane perpendicular to a longitudinal axis of a rod channel of the receiving part and extending through centers of the legs of the receiving part.
Figure 17:
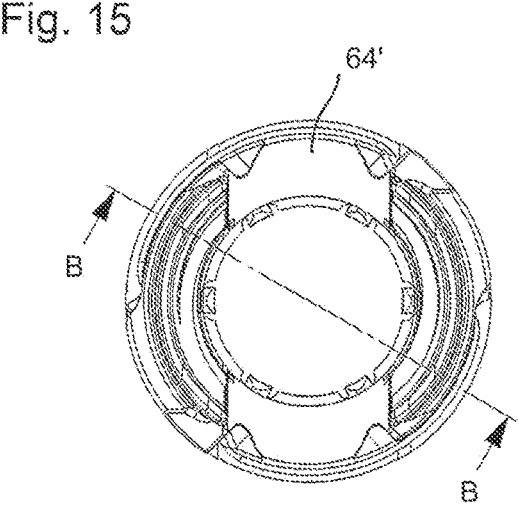
FIG. 17 shows a top view of the coupling device of FIG. 16.

Referring further to FIG. 15, a monolithic unit 70' including the receiving part 50' and the locking member 60' will be described. As in the first embodiment, the locking member 60' and the receiving part 50' can be manufactured as one part using an additive layer manufacturing technique. The monolithic unit 70' includes a holding portion 71' that is monolithically connected to the locking member 60' and to the receiving part 50'. The holding portion 71' is substantially sleeve-shaped, and an upper end 71a of the sleeve continues into the locking member 60'. For example, the upper end 71a may be thickened and may continue into the projection 63', and simultaneously into the bottom end 5b of the receiving part 50'. The integrated unit including the locking member 60' and the receiving part 50' is obtained or otherwise formed by holding the monolithic unit 70' at the holding portion 71' and cutting away the upper end 71a of the monolithic unit 70', so that as a result, the locking member 60' and the receiving part 50' are movable relative to each other but cannot be separated from each other. The internal thread 56' in the passage of the receiving part 50' may preferably be formed conventionally by thread cutting after manufacturing the monolithic unit 70' or after cutting away the integrated unit from the holding portion 71'.

In use, the pressure member 30 is pre-assembled with the integrated unit. In contrast to the first embodiment, the locking member 60' can be moved upward from a first position in which the pressure member 30 is in an insertion position that permits insertion of the head 3 into the head receiving section 31, to a second position in which the projections 63' enter or enter farther into the recesses 502 to exert pressure onto the outer surface of the lower narrowing portion 33 of the pressure member 30. The head 3 is prevented from removal and can optionally be provisionally held by friction in the pressure member. Final locking of the head 3 can be achieved by inserting the rod 100 and exerting pressure with the fixation member 8' onto the rod and via the pressure member 30 onto the head 3.

A third embodiment of the polyaxial bone anchoring device will be described with reference to FIGS. 19 to 24. Parts and portions that are identical or similar to the first and second embodiments are indicated with the same reference numerals, and the descriptions thereof are not repeated. The receiving part 50" in this embodiment is a two-part member, and the locking member 60" is a separate ring that is interconnected with the two parts of the receiving part, such that the locking member holds the two parts together in such a manner that none of the parts can be removed or separated from the others without damaging or destroying the integrated unit. As can be seen in particular in FIGS. 20, 23, and 24, the substantially cylindrical receiving part 50" includes two similar halves 50a", 50b" that are mirror-symmetrical relative to a plane spanned by the central axis C and a longitudinal axis of the rod channel. Each half 50a", 50b" has a head receiving portion 505, wherein the head receiving portions 505 together form a seat for the head 3 of the bone anchoring element, as shown in FIGS. 23 and 24. Moreover, each of the halves 50a", 50b" defines half of a passage 511 that extends completely through the receiving part from the top end 5a to the bottom end 5b, and half 504 of a substantially U-shaped recess defining a rod channel, so that, similar to the first embodiment, each half 50a", 50b" defines a leg 515 of the receiving part 50". Circumferentially outer edges of the head receiving portions 505 up to a bottom of the substantially U-shaped recess 504 are formed such that when the halves 50a", 50b" are put together, the edges have only a limited contact region 510. As a result, the two halves 50a", 50b" can be slightly tilted relative to each other from a first position that permits the insertion of the head 3 to a second position in which the head 3 is clamped or finally locked.

At the outer surface of the halves 50a", 50b", two circumferentially extending grooves 507 are formed that are configured to accommodate a ring shaped portion of the locking member 60". The size and shape of the grooves 507 is such that the locking member 60" is substantially restricted from moving in the axial direction but is able to move in the circumferential direction, i.e., the locking member can be rotated.

The locking member 60" is a separate ring that fits into the groove 507. The locking member has two extensions 600 that are offset by 180° and that extend from the outer surface of the ring downward towards the bottom end 5b of the receiving part 50". Also, the extensions are thinner in the radial direction and may be inwardly inclined so that a distance between the extensions narrow with respect to the central axis C as the extensions extend down towards the bottom end 5b.

The receiving part 50" further defines, on its outer surface at two opposite positions offset by 180°, a groove with limited length, or in other words a pocket 508, that extends in the circumferential direction from a position that is closer to the rod channel to a position at or near a middle of the legs 515. The grooves 508 are configured to receive the extensions 600 of the locking member 60", respectively. A bottom of the groove 508 forms a ramp, by means of which the depth of the groove 508 decreases towards the middle of the legs 515. In contrast to the recesses 505 for the head and 504 for the rod, the grooves 508 with the ramp are not mirror-symmetrical relative to the plane defined by the central axis C and the longitudinal axis of the rod channel. Rather, the position and the orientation of the ramps are such that, when the locking member 60" is rotated, the extensions 600 move along the ramp towards the middle of the legs 515, thereby pressing the two halves 50a", 50b" in the region of the spherical recesses 505 against each other, so that an inserted head 3 cannot be removed and can be clamped and finally locked.

As shown in FIGS. 21 and 23, the locking member is in a first position in which the extensions 600 are spaced apart from the bottom of the groove 508. As a result, the head receiving recesses 505 can slightly spread apart to permit insertion of the head 3. As shown in FIGS. 22 and 24, the locking member 60" has been rotated to a second position in which the extensions 600 press against the bottom of the groove 508. Thereby the head receiving recesses 505 are pressed together to clamp or lock the head.

Moreover, the receiving part 50" defines circumferential recesses 56" for receiving a fixation assembly 8 similar to the fixation assembly used in the first embodiment. Furthermore, tool engagement recesses 512 may be provided on each of the legs at a distance from the top end 5a of the receiving part 50".

Figure 25:
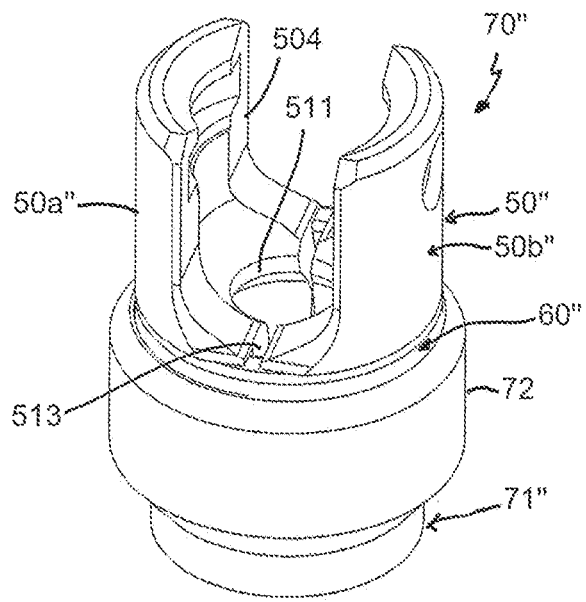
FIG. 25 shows a perspective view from a top of a monolithic unit including the receiving part and the locking member of the coupling device according to the third embodiment of FIGS. 19 to 24, the monolithic unit further including a holding portion.
Figure 26:
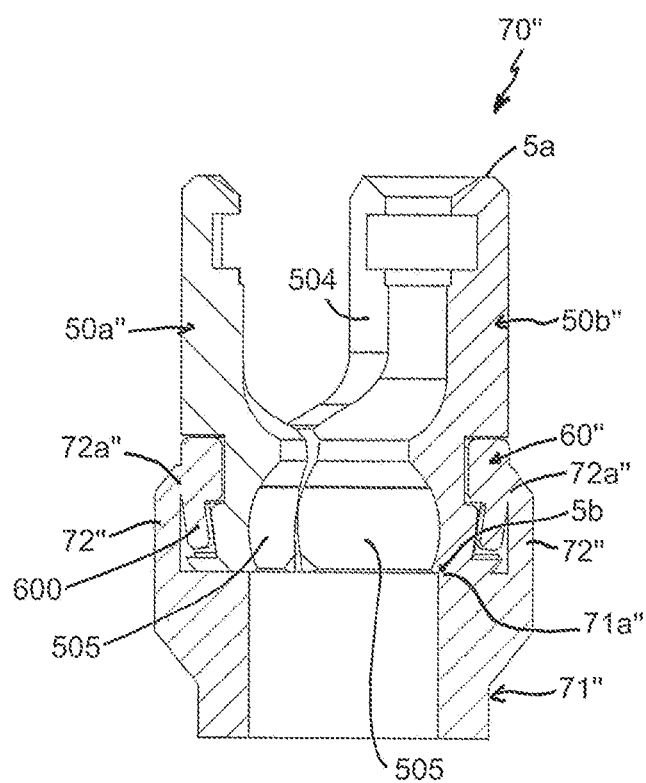
FIG. 26 shows a cross-sectional view of the monolithic unit of FIG. 25, wherein the cross-section is taken in a plane including the central axis of the coupling device and arranged at an angle relative to the longitudinal axis of the rod channel.
Figure 27:
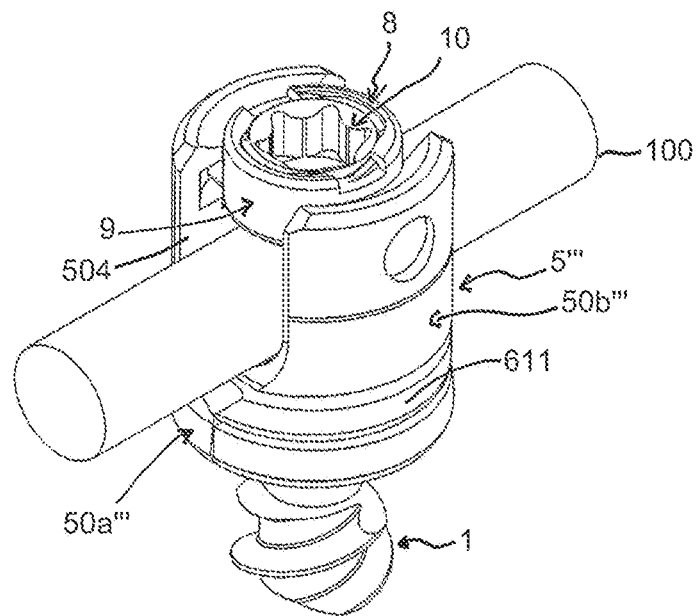
FIG. 27 shows a perspective view of a fourth embodiment of the polyaxial bone anchoring device with a fourth embodiment of the coupling device.
Figure 28:
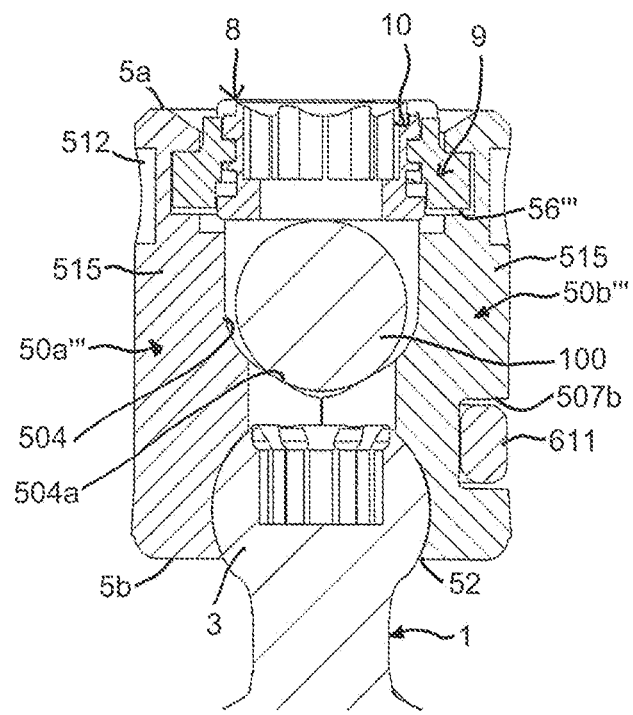
FIG. 28 shows a cross-sectional view of the polyaxial bone anchoring device of FIG. 27, the cross-section taken in a plane perpendicular to a longitudinal axis of an inserted rod and extending through centers of legs of a receiving part of the coupling device.
Figure 29:
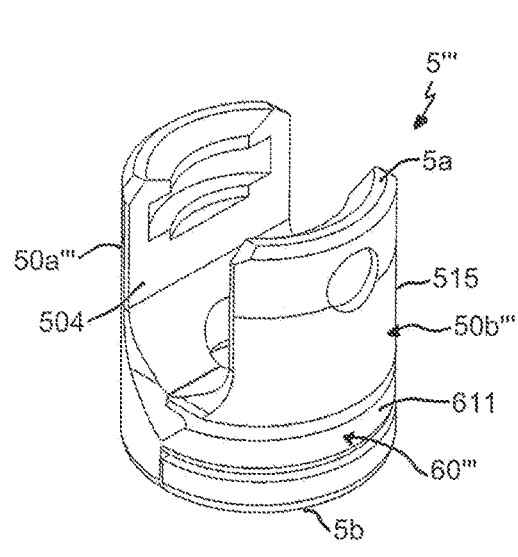
FIG. 29 shows a perspective view from a top of the coupling device according to the fourth embodiment.
Figure 30:
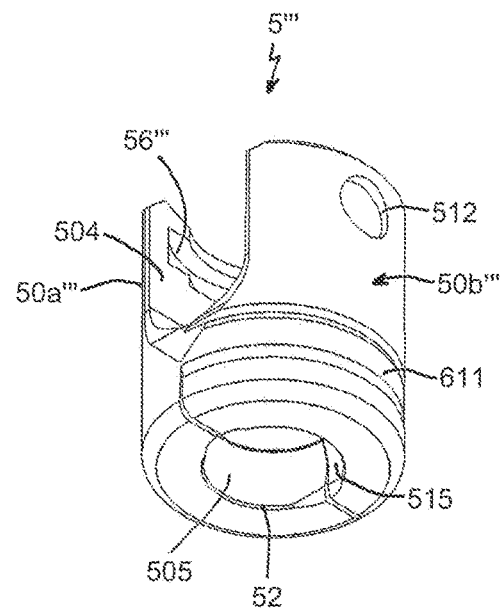
FIG. 30 shows a perspective view from a bottom of the coupling device of FIG. 29.
Figure 31:
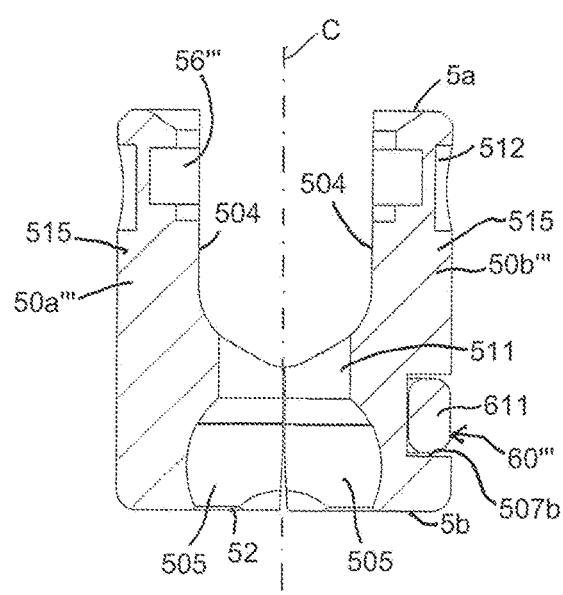
FIG. 31 shows a cross-sectional view of the coupling device of FIGS. 29 and 30, the cross-section taken in a plane including a central axis of the receiving part and extending through centers of legs of the receiving part.

The coupling device is preferably manufactured using an additive layer manufacturing technology similarly as described in the previous embodiments. Referring to FIGS. 25 and 26, a monolithic unit 70" is shown that includes the receiving part 50" and the locking member 60" as a single part. The monolithic unit 70" further includes a holding portion 71" that is substantially sleeve-shaped. An upper surface 71a of the holding portion is monolithically formed with the lower end 5b of the two halves of the receiving part 50". From the upper surface, a monolithic connection via a rib 72" is made to the outside of the locking member 60". Hence, the holding portion 71" is connected at two portions with the receiving part 50" and the locking member 60". The integrated unit including the receiving part 50" and the locking member 60" is obtained by cutting away the holding portion 71" at the position of the lower end 5b of the receiving part 50" and at a position 72a" at the outside of the ring portion of the locking member 60". The locking member 60" cannot fall apart or be otherwise separated from the receiving part 50" since the locking member is held in the grooves 507, 508.

Figure 20:
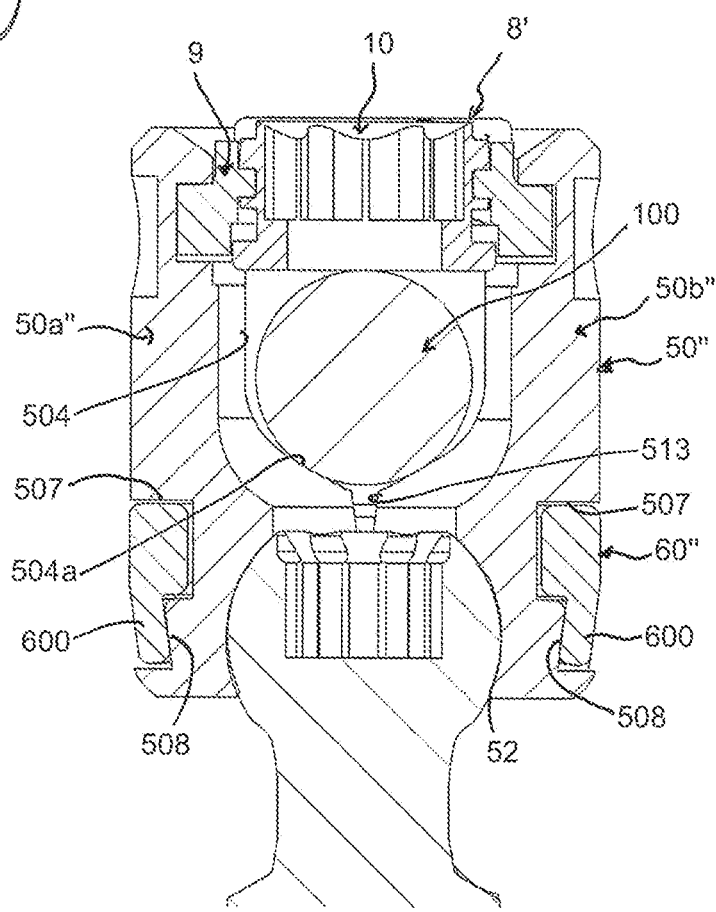
FIG. 20 shows a cross-sectional view of the polyaxial bone anchoring device of FIG. 19, the cross-section taken in a plane extending perpendicular to a longitudinal axis of an inserted rod and extending through center of legs of a receiving part of the coupling device.

In use, the coupling device is mounted onto the head 3 of the bone anchoring element 1 with the locking member 60" in the first position. Then, the locking member 60" is rotated, for example, with an instrument, so that the extensions 600 move along the ramp until the locking member 60" is in the second position. This results in pressing the two halves 50a", 50b" of the receiving part 50" together so that the head receiving portions 505 enclose and clamp the head 3. As shown in FIG. 20, when the head 3 is locked between the two halves, there may be a gap 513 between the two halves 50a", 50b" at the bottom 504a of the recess 504. Inserting the rod 100 and fixing the rod with the second member 10 may exert an additional force onto the two halves that further locks the head 3.

Referring to FIGS. 27 to 32, a fourth embodiment of the bone anchoring device and the coupling device will be described. Parts and portions of the fourth embodiment that are identical or similar to those of the previous embodiments are indicated with the same reference numerals, and the descriptions thereof will not be repeated. The coupling device 5'" according to the fourth embodiment differs from the coupling device 5" according to the third embodiment in that the locking member 60'" is monolithically formed with one of the halves of the receiving part. In addition, the pockets 508 and the extensions 600 of the third embodiment are not necessary. In greater detail, the receiving part 50'" includes, similarly to the second embodiment, a first half 50a'" and an opposite second half 50b'" which is at least partially mirror-symmetrical to a plane spanned by the central axis C and the longitudinal axis of the rod channel, for example, portions of the halves forming the head receiving portion 505 and the rod support 504a. Each of the halves 50a'", 50b'" includes a head receiving portion 505, a recess 504, and a half of a passage 511 that respectively form the seat for the head, the rod channel, and the passage. The second half 50b'" defines, at a distance from the lower end 5b, a groove 507b. The first half 50a'" is monolithically connected to a half of a ring 611 that extends around the second half 50b'" in the groove 507b. The dimensions of the groove 507b and the ring 611 are such that the two halves 50a'", 50b'" can be slightly tilted against each other. The half of the ring 611 together with the first half 50a'" forms a locking member 60'". The locking member 60'" can assume a first position in which the head 3 can be inserted into the head receiving portion 505 through the lower opening 52 and a second position in which the first half 50a'" is tilted with respect to the second half 50b'" to an extent such that an inserted head 3 cannot be removed from the head receiving portion 505. At a distance from the top end 5a, a circumferentially extending recess 56'" is provided on each of the legs that serves to receive the fixation assembly 8, which may be identical to the fixation assembly used in the first embodiment.

In use, after insertion of the rod 100 and the fixation assembly, tightening of the fixation assembly 8 results in pressure exerted by the rod onto the bottom 504a of the recess 504. Thereby the two halves 50a'", 50b'" are pressed together in the region of the head receiving portion 505 so that an inserted head 3 cannot be removed and can be finally locked.

Figure 32:
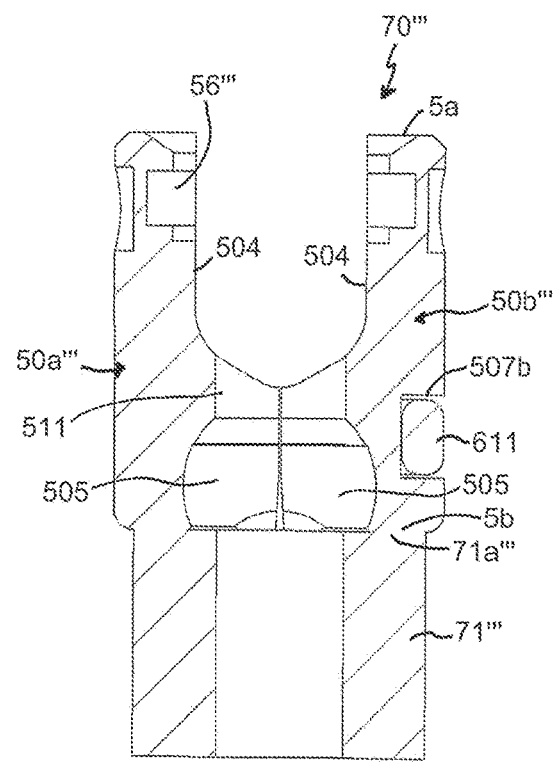
FIG. 32 shows a cross-sectional view of a monolithic unit including the receiving part and a locking member according to the fourth embodiment, the monolithic unit further including a holding portion, the cross-section taken in a plane extending perpendicular to a longitudinal axis of a rod channel of the receiving part and through centers of the legs of the receiving part.

The two halves 50a", 50b" are manufactured as a monolithic unit 70'", as shown in FIG. 32. As in the previous embodiments, a holding portion 71'" is provided that is substantially sleeve-shaped and is connected with its upper end 71a'" to the first half 50a'" and to the second half 50b'" at a position of the lower end 5b of the receiving part 50". The integrated unit includes the two halves 50a'", 50b'", wherein the first half 50a'" including the locking member 60'" is obtained by cutting the monolithic unit at a position corresponding to the lower end 5b of the receiving part 50'".

Further modifications of the above described embodiments are also conceivable. In particular, the shape of the parts is not limited to the detailed shapes shown in the figures. Deviations may be possible and encompassed by the disclosure. It shall be noted that the features of one embodiment can be also combined with features of other embodiments. For example each of the receiving parts may have extended tabs. Instead of the fixation assembly, a single set screw may be used in all of the embodiments, or vice versa. For the bone anchoring element, all types of bone anchoring elements that are suitable for anchoring in bone or vertebra may be used, in particular, also bone nails.

The rod may also have various shapes and/or varying cross-sections along its length. The rod may be stiff or more flexible.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:
1. A coupling device for coupling a rod to a bone anchoring element, the coupling device comprising:
   a receiving part having a first end and a second end below the first end, and comprising a head receiving portion defining an accommodation space for receiving a head of the bone anchoring element, a rod receiving portion defining a recess for receiving the rod, a downwardly facing surface, and an upwardly facing surface below and monolithically formed with the downwardly facing surface; and a locking member movable relative to the receiving part from a first position where the head is insertable into the head receiving portion to a second position where a maximum size of an opening at the second end of the receiving part is reduced to prevent the head from being removed from the head receiving portion;

wherein at least part of the locking member is held to the receiving part between the downwardly and upwardly facing surfaces, and wherein the receiving part and the locking member are only separable from one another by permanently deforming or damaging at least one of the receiving part or the locking member.

2. The coupling device of claim 1, wherein the locking member forms at least part of a ring that extends around the receiving part.

3. The coupling device of claim 1, wherein the accommodation space forms a seat configured to hold and allow pivoting of the head relative to the seat.

4. The coupling device of claim 3, wherein the seat is radially compressible to clamp the head.

5. The coupling device of claim 1, wherein the locking member defines a seat configured to hold and allow pivoting of the head relative to the seat, wherein the seat extends around a portion of the head with a greatest outer width.

6. The coupling device of claim 1, further comprising a separate compression member positionable in the receiving part that defines a seat configured to hold and allow pivoting of the head relative to the seat.

7. The coupling device of claim 1, wherein the locking member comprises a support surface for the rod.

8. The coupling device of claim 1, wherein the receiving part comprises at least two separate portions, and wherein the locking member holds the at least two portions of the receiving part together.

9. The coupling device of claim 8, wherein the locking member is monolithic with at least one of the at least two portions.

10. The coupling device of claim 8, wherein the at least two portions are tiltable relative to each other to move the locking member from the first position to the second position.

11. The coupling device of claim 1, wherein the locking member is rotatable around the receiving part from the first position to the second position.

12. The coupling device of claim 1, wherein the recess for the rod defines two legs, and wherein the coupling device further comprises a fixation assembly engageable with the legs to fix the rod relative to the receiving part.

13. The coupling device of claim 12, wherein the fixation assembly comprises a first member and a second member movable relative to the first member, wherein the first member is configured to be held between the legs in a thread-free manner.

14. A coupling device for coupling a rod to a bone anchoring element, the coupling device comprising:

a receiving part comprising a head receiving portion defining an accommodation space for receiving a head of the bone anchoring element and a rod receiving portion defining a recess for receiving the rod; and a locking member movable relative to the receiving part from a first position where the head is insertable into the head receiving portion to a second position where a maximum size of an opening at the second end of the receiving part is reduced to prevent the head from being removed from the head receiving portion;

wherein the locking member is formed at a position relative to the receiving part where a first abutting surface of the receiving part prevents axial movement of the locking member in a first direction and a second abutting surface of the receiving part prevents axial movement of the locking member in a second direction opposite the first direction, and wherein the receiving part and the locking member are only separable from one another by permanently deforming or damaging at least one of the receiving part or the locking member.

15. The coupling device of claim 14, wherein the receiving part and the locking member are formed together as an integrated unit.

16. The coupling device of claim 15, wherein the integrated unit is formed as a monolithic unit that is then separable at at least one location to form the receiving part and the locking member.

17. The coupling device of claim 16, wherein the monolithic unit further comprises a holding portion that is removed when the monolithic unit is separated to form the receiving part and the locking member.

18. The coupling device of claim 14, wherein the receiving part and the locking member are formed by an additive manufacturing method.

19. The coupling device of claim 18, wherein the additive manufacturing method comprises a powder based additive layer manufacturing method.

20. A method of coupling a rod to a bone via a bone anchoring device comprising a bone anchoring element comprising a shank and a head, a receiving part having a first end and a second end below the first end, and comprising a head receiving portion defining an accommodation space for receiving a head of the bone anchoring element, a rod receiving portion defining a recess for receiving the rod, a downwardly facing surface, and an upwardly facing surface below and monolithically formed with the downwardly facing surface, a locking member, wherein at least part of the locking member is held to the receiving part between the downwardly and upwardly facing surfaces, and wherein the receiving part and the locking member are only separable from one another by permanently deforming or damaging at least one of the receiving part or the locking member, and a fixation assembly, the method comprising:

anchoring the shank of the bone anchoring element to bone;

inserting the head of the bone anchoring element into the head receiving portion when the locking member is at a first position relative to the receiving part;

adjusting the locking member from the first position to a second position where a maximum size of an opening at the second end of the receiving part is reduced to prevent the head from being removed from the head receiving portion;

adjusting an angular position of the receiving part relative to the head;

inserting the rod into the recess of the rod receiving portion; and advancing the fixation assembly in the recess of the rod receiving portion to lock the rod and the angular position of the head relative to the receiving part.

* * * * *

UNITED STATES PATENT AND TRADEMARK OFFICE
CERTIFICATE OF CORRECTION

PATENT NO. : 11,717,329 B2
APPLICATION NO. : 17/879685
DATED : August 8, 2023
INVENTOR(S) : Timo Biedermann et al.

Page 1 of 1

It is certified that error appears in the above-identified patent and that said Letters Patent is hereby corrected as shown below:

In the Specification
Column 15, Line 57   Delete "5′′′′" and
Insert -- 5′′ ′ --

Signed and Sealed this
Twenty-fourth Day of October, 2023

Katherine Kelly Vidal
*Director of the United States Patent and Trademark Office*